(12) United States Patent
Gray et al.

(10) Patent No.: US 12,076,134 B2
(45) Date of Patent: Sep. 3, 2024

(54) POSTURE ANALYSIS SYSTEMS AND METHODS

(71) Applicant: Brightday Technologies, Inc., San Francisco, CA (US)

(72) Inventors: Richard William Bow Gray, San Francisco, CA (US); Jens-Peter Jungclaussen, San Francisco, CA (US); Jonas P. Cleveland, Philadelphia, PA (US); James Morris, San Francisco, CA (US)

(73) Assignee: Brightday Technologies, Inc., San Francisco, CA (US)

( * ) Notice: Subject to any disclaimer, the term of this patent is extended or adjusted under 35 U.S.C. 154(b) by 79 days.

(21) Appl. No.: 17/673,499

(22) Filed: Feb. 16, 2022

(65) Prior Publication Data

US 2022/0167878 A1  Jun. 2, 2022

Related U.S. Application Data

(62) Division of application No. 15/650,592, filed on Jul. 14, 2017, now Pat. No. 11,311,210.

(60) Provisional application No. 62/362,391, filed on Jul. 14, 2016.

(51) Int. Cl.
*A61B 5/11* (2006.01)
*A61B 5/00* (2006.01)
*A61B 5/103* (2006.01)

(52) U.S. Cl.
CPC .......... *A61B 5/1116* (2013.01); *A61B 5/1036* (2013.01); *A61B 5/743* (2013.01); *A61B 5/7455* (2013.01); *A61B 5/486* (2013.01); *A61B 2562/0219* (2013.01)

(58) Field of Classification Search
None
See application file for complete search history.

(56) References Cited

U.S. PATENT DOCUMENTS

2006/0045312 A1* 3/2006 Bernstein ........... A63B 24/0003
                                                    382/209
2009/0324024 A1* 12/2009 Worthington ........ G06V 40/161
                                                    382/118

OTHER PUBLICATIONS

Menard et al. Anchorage's Approach to Real-Time Snowplow Tracking; 2012 15th International IEEE Conference on Intelligent Transportation Systems Anchorage, Alaska, USA, Sep. 16-19, 2012 (Year: 2012).*

Taieb-Maimon et al. The effectiveness of a training method using self-modeling webcam photos for reducing musculoskeletal risk among office workers using computers; 2012 Applied Ergonomics 43 (2012) 376-385 (Year: 2012).*

* cited by examiner

*Primary Examiner* — Jay B Shah

(74) *Attorney, Agent, or Firm* — David R. Stevens; Stevens Law Group

(57) ABSTRACT

Example posture analysis systems and methods are described. In one implementation, a computing system identifies a deviation of a user's posture from a predetermined posture based on visual data associated with the user. The user is informed of the deviation via a graphical image displayed on a display device. The user is then provided with instructions for correcting the deviation via the graphical image displayed on the display device.

21 Claims, 20 Drawing Sheets

POSTURE ANALYSIS SYSTEMS AND METHODS

RELATED APPLICATION

This application is a divisional of U.S. application Ser. No. 15/650,592, entitled "Posture Analysis Systems and Methods," filed Jul. 14, 2017, which claims the priority benefit of U.S. Provisional Application Ser. No. 62/362,391, entitled "Tracking and Correcting Posture of a User," filed on Jul. 14, 2016, the disclosures of both are hereby incorporated by reference herein in their entirety.

TECHNICAL FIELD

The present disclosure relates to systems and methods that analyze and track a user's posture.

BACKGROUND

In many situations, people spend significant amounts of time in front of desktop computers, laptop computers, display screens, or sitting in particular chairs or other seating devices. Long hours in these types of situations may be associated with unhealthy posture habits, which the person may be unaware of. In contrast, having a good posture may allow a person to avoid certain problems associated with sitting, standing, or other positions with an incorrect posture.

Incorrect posture can cause problems a person's spine, back or neck which may result in pain or other problems. In some situations, health may be improved if proper posture is attained. There exists a need for a system that helps a user maintain proper posture in a variety of situations.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

DETAILED DESCRIPTION

Figure 1A:
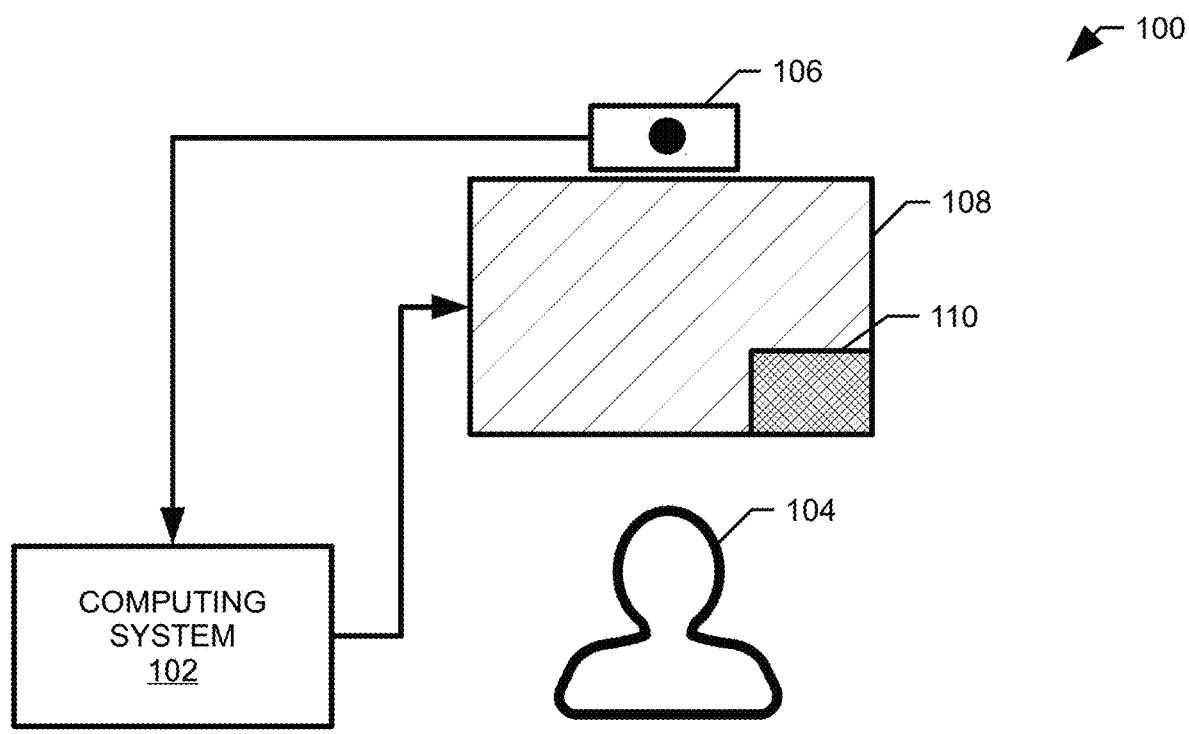
FIG. 1A is a block diagram depicting an embodiment of a posture analysis system.

In the following description, reference is made to the accompanying drawings that form a part thereof, and in which is shown by way of illustration specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, databases, or characteristics may be combined in any suitable combinations and/or sub-combinations in one or more embodiments or examples. In addition, it should be appreciated that the figures provided herewith are for explanation purposes to persons ordinarily skilled in the art and that the drawings are not necessarily drawn to scale.

Embodiments in accordance with the present disclosure may be embodied as an apparatus, method, or computer program product. Accordingly, the present disclosure may take the form of an entirely hardware-comprised embodiment, an entirely software-comprised embodiment (including firmware, resident software, micro-code, etc.), or an embodiment combining software and hardware aspects that may all generally be referred to herein as a "circuit," "module," or "system." Furthermore, embodiments of the present disclosure may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages. Such code may be compiled from source code to computer-readable assembly language or machine code suitable for the device or computer on which the code will be executed.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction and then scaled accordingly. A cloud model can be composed of various characteristics (e.g., on-demand self-service, broad network access, resource pooling, rapid elasticity, and measured service), service models (e.g., Software as a Service ("SaaS"), Platform as a Service ("PaaS"), and Infrastructure as a Service ("IaaS")), and deployment models (e.g., private cloud, community cloud, public cloud, and hybrid cloud).

The flow diagrams and block diagrams in the attached figures illustrate the architecture, functionality, and operation of possible implementations of systems, methods, and computer program products according to various embodiments of the present disclosure. In this regard, each block in the flow diagrams or block diagrams may represent a module, segment, or portion of code, which includes one or more executable instructions for implementing the specified logical function(s). It will also be noted that each block of the block diagrams and/or flow diagrams, and combinations of blocks in the block diagrams and/or flow diagrams, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow diagram and/or block diagram block or blocks.

The systems and methods described herein disclose a system that, using visual data, interactively monitors and tracks a user's posture in substantially real time, and offers feedback to the user in substantially real time if the user's posture deviates beyond a certain extent from a predetermined posture. This system can be implemented on a computing system such as a laptop computer or a desktop computer, and includes an imaging device such as a webcam or a video camera to acquire the visual data. Feedback to the user may be displayed on, for example, a computer monitor or any other visual display device. Machine learning methods and software libraries such as OpenCV may be used to implement certain components of the posture analysis systems described herein.

FIG. 1A is a block diagram depicting an embodiment of a posture analysis system 100. In some embodiments, posture analysis system includes a computing system 102 that may be a laptop computer, a desktop computer, a mobile device, a tablet, or any other computing device or processing device capable of performing the functions and operations discussed herein. In some embodiments, computing system 102 may be remotely located, for example as a part of a cloud computing system. Computing system 102 is configured to receive visual data from an imaging device 106 that may be a webcam, a video camera, a digital still image camera, or any other imaging device capable of capturing or identifying an image. Visual data received by computing system 102 from imaging device 106 may be any combination of video data, still images, infrared images and so on.

Computing system 102 is also configured to output visual data to a display device 108 that may be an LCD display, an OLED display, a CRT display, or any other display device. In some embodiments, imaging device 106 may be attached to display device 108 and may be physically oriented to capture visual data associated with a user 104. As used herein, "visual data" includes data such as digital video, digital still images, infrared images, and the like. In some embodiments, the visual data includes at least a portion of the user within an image frame from any angle or perspective associated with imaging device 106. In other embodiments, imaging device 106 may be integrated into display device 108 (e.g. a webcam), such that user 104 is within the field of view of imaging device 106 when looking at display device 108. In other words, imaging device 106 is configured to capture an image of at least a portion of user 104 while user 104 performs one or more specific tasks on computing system 102. In some embodiments, user 104 may position themselves such that the optical axis of imaging device 106 is substantially orthogonal to the left pectoral muscle and right pectoral muscle of user 104.

In some embodiments, the operation of posture analysis system 100 consists of two steps. A first step is an initialization step where user 104 assumes a predetermined posture that is captured by imaging device 106 and stored by computing system 102. In some embodiments, the term "predetermined posture" may be defined as a posture used to initialize posture analysis system 100 and used as a basis for tracking a current posture of the user. In some embodiments, the term "predetermined posture" may be also referred to as a "reference posture," a "preferred posture," a "healthy posture," a "good posture," and so on. For example, the predetermined posture may be an ideal or preferred posture for the particular user. In particular embodiments, image processing techniques such as computer vision, facial detection and facial recognition may be used in conjunction with machine learning algorithms to analyze and appropriately characterize the visual data received by computing system 102. In some embodiments, computer vision software libraries, such as OpenCV, may be used to implement certain functions of posture analysis system 100, such as analysis of visual data.

In some embodiments, a second step associated with the operation of posture analysis system 100 is a tracking step where a current posture of user 104 is tracked by computing system 102 in substantially real time based on visual data received from imaging device 106. In some embodiments, the term "substantially real time" includes operation with a small time delay such as a few seconds or a fraction of a second. In other embodiments, substantially real time may include operation with a longer time delay up to several minutes. In particular embodiments, a temporal history associated with the tracking of the posture of user 104 may be stored and presented to the user at a later time (for example, on display device 108 or via email).

In some embodiments, the current posture of user 104 is tracked relative to the predetermined posture. In some situations, if the tracked current posture of user 104 deviates from the predetermined posture by more than a certain threshold, computing system 102 may inform user 104 about the deviation via a graphical image 110 displayed on display device 108. In some embodiments, user 104 may be informed about the deviation via graphical image 110 in substantially real time. In particular embodiments, graphical image 110 may simultaneously include an image depicting the predetermined posture, an image depicting the current posture of user 104, and information that may allow user 104 to substantially eliminate the deviation and return to the predetermined posture. In some embodiments, information presented in graphical image 110 may be any combination of graphical symbols, textual information and a video rendering of user 104. If user 104 follows the presented information to eliminate the deviation and assumes the predetermined posture again (i.e., if user 104 corrects their posture), computing system 102 may detect that user 104 has assumed the predetermined posture based on the visual data, and may then remove graphical image 110 from display device 108. Details of the initialization and tracking steps are discussed in greater detail herein.

In some embodiments, computing system 102 may associate the current posture of user 104 with a specific task being performed by user 104. In particular embodiments, computing system 102 may associate a deviation of the posture of user 104 from the predetermined posture with a specific task being performed by user 104. In some embodiments, the task being performed by user 104 is an activity being performed by user 104. Examples of the task being performed by the user include using an application executing on computing system 102, reading a book, writing, riding in a vehicle, performing surgery in an operating room, practicing yoga, or any other kind of activity. Posture analysis system 100 may be used in a variety of situations such as operating rooms, airplanes (to ensure a passenger assumes a healthy posture), cars, and so on.

Figure 1B:
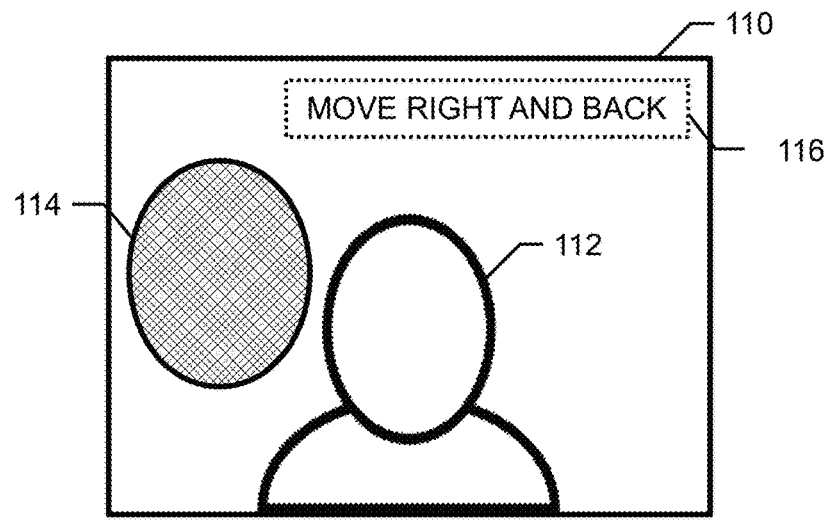
FIG. 1B is a block diagram depicting an embodiment of a graphical image as displayed by a posture analysis system.

FIG. 1B is a block diagram depicting an embodiment of a graphical image 110 as displayed by a posture analysis system 100. In some embodiments, graphical image 110 may include a line drawing of a predetermined posture 112, and a graphic element 114 corresponding to the current posture of user 104. In some embodiments, graphic element 114 may be an ellipse that corresponds to a position of the face of user 104 in a frame associated with the visual data as determined by facial detection algorithms running on computing system 102. In some embodiments, graphic element 114 may be a polygon. In particular embodiments, graphic element 114 may be any combination of a cartoon character, a photographic depiction of a head, shoulders and a body, a three-dimensional mesh rendering of a head, shoulders and a body, a cut-out rendition of the face of user 104 on a comical background, an image of another person, an animal (e.g., a bunny), and the like. In some embodiments, graphical image 110 may be generated by computing system 102 and rendered on display device 108 in substantially real time.

The position of graphic element 114 in graphical image 110 correlates with a spatial position of the face of user 104 which, in turn, can be mapped to the current posture associated with user 104. In some embodiments, graphical image 110 may also include a text box 116 that provides posture correction information to user 104. If user 104 follows the posture correction information, user 104 can be guided back to assume the predetermined posture. FIG. 1B depicts text box 116 as informing user 104 to move right and back (i.e., away from display device 108) to achieve the predetermined posture. Further details of the posture correction step that involve substantially eliminating a deviation associated with a user's current posture from the predetermined posture are provided herein.

Figure 2:
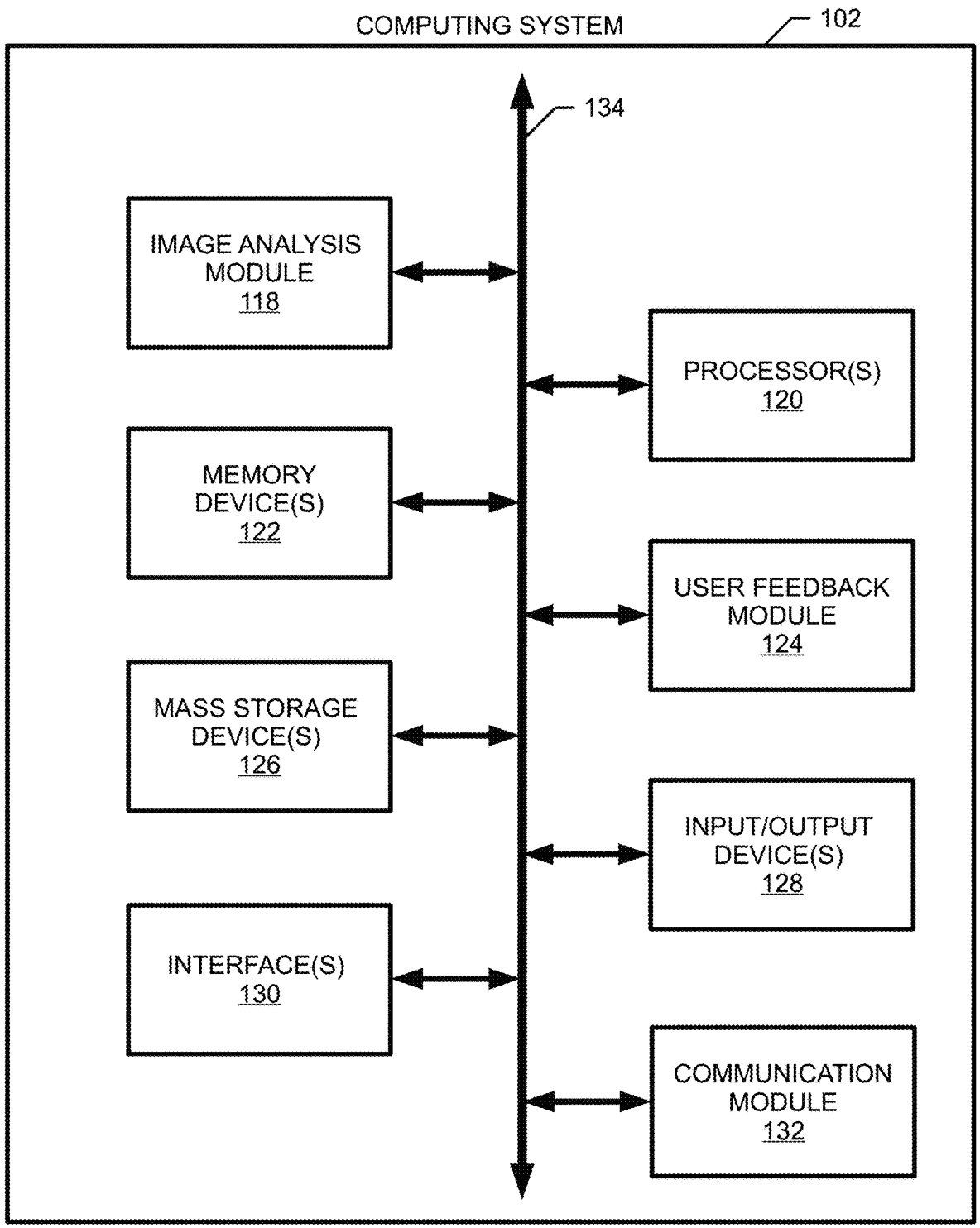
FIG. 2 is a block diagram depicting an embodiment of a computing system capable of implementing a posture analysis system.

FIG. 2 is a block diagram depicting an embodiment of computing system 102 capable of implementing posture analysis system 100. In some embodiments, computing system 102 may include an image analysis module 118 that is configured to process visual data received from imaging device 106. In some embodiments, image analysis module 118 may implement at least one software algorithm such as facial recognition, facial detection, machine learning, computer vision, and so on when analyzing the visual data. In particular embodiments, image analysis module 118 may use software libraries for computer vision, such as OpenCV. Image analysis module 118 may be configured to detect a user's face and other parts of the user's body, such as the user's shoulders based on visual data received from imaging device 106. In some embodiments, image analysis module 118 may be configured to compare a current user posture with a predetermined posture and compute a deviation associated with the current user posture from the predetermined posture. Further details of image analysis module 118 are provided herein.

In some embodiments, computing system 102 includes one or more processors 120 that are configured to perform processing functions that include, but are not limited to, mathematical and arithmetic computations or any other computational functions. One or more processors 120 may be any combination of microprocessors, microcontrollers, digital signal processors (DSPs), field-programmable gate arrays (FPGAs), or any other processing devices. Computing system 102 may also include one or more memory devices 122 that are configured to store data in any combination of volatile or non-volatile formats. Examples of memory devices 122 include random access memory (RAM), read-only memory (ROM), NAND flash memory, and so on.

In some embodiments, computing system 102 may include a user feedback module 124 that is configured to generate feedback associated with a user's posture to the user when a deviation in the user's posture relative to the predetermined posture is above a certain threshold. Details of user feedback module 124 are provided herein. In some embodiments, computing system 102 may include one or more mass storage devices 126, that include any combination of magnetic hard disk drives, solid-state drives, or any other type of storage mechanism. Mass storage devices 126 may be configured to store data in a non-volatile format for access at a later time.

One or more input/output devices 128 may also be included in computing system 102. In some embodiments, input/output devices 128 may include any combination of keyboards, computer mice, computer video terminals or screens, audio input/output devices (microphones and speakers), touchscreens, or any other device that allows a user to interact with computing system 102.

Computing system 102 may also include one or more interfaces 130 that are configured to allow coupling between processing system 102 and other external devices. Interfaces 130 may include, for example, one or more universal serial bus (USB) ports, IEEE 1394 (Firewire) ports, IEEE 802.11 (WiFi) interfaces, Bluetooth interfaces, and the like.

In some embodiments, computing system 102 may include a communication module 132 that is configured to communicate, for example, with imaging device 106, display device 108, and any other components, systems, devices, or routines. In some embodiments, communication module 132 may be responsible for implementing different communication protocols associated with different devices.

In some embodiments, the different subcomponents of computing system 102 as described herein may each be coupled to a central data bus 134 that is configured to transmit communication signals and data between the different subcomponents of computing system 102.

Figure 3:
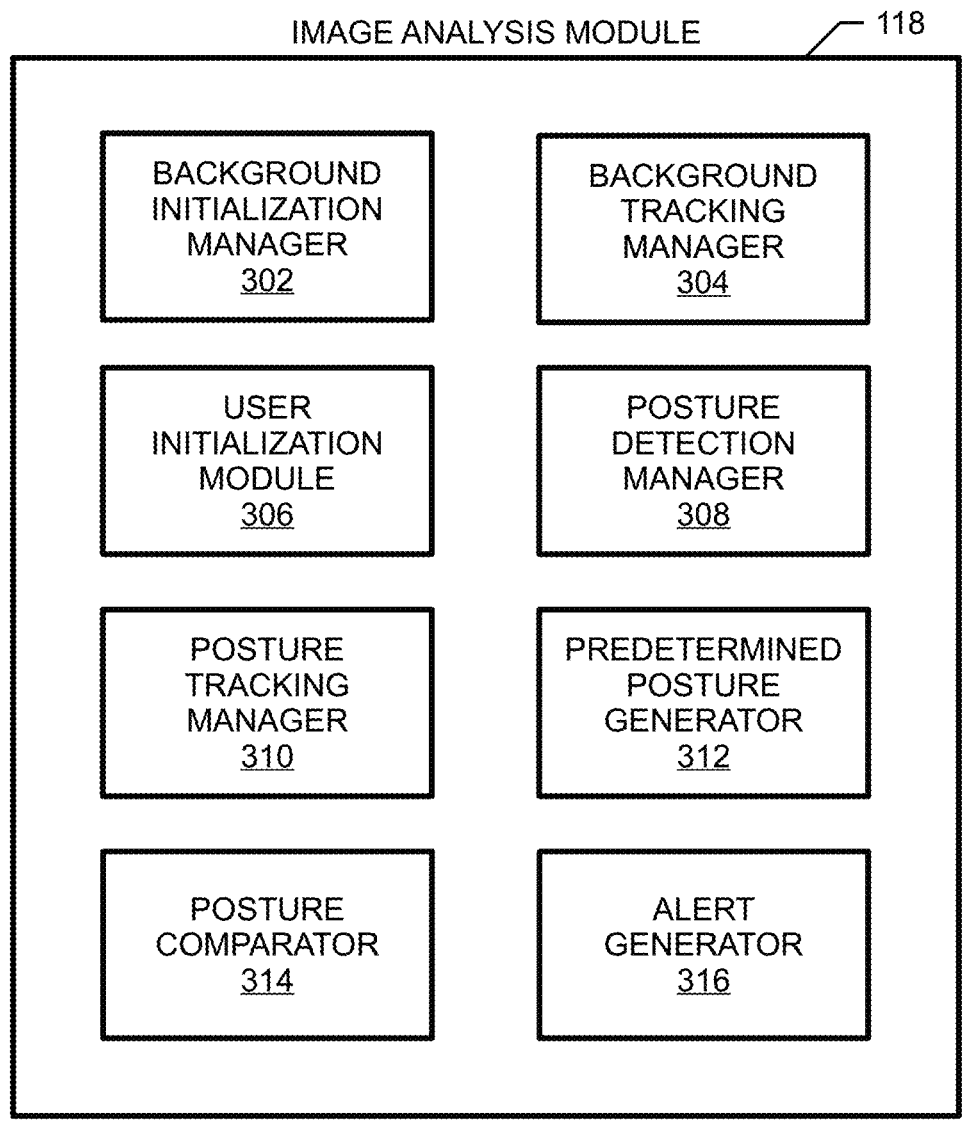
FIG. 3 is a block diagram depicting an embodiment of an image analysis module.

FIG. 3 is a block diagram depicting an embodiment of image analysis module 118. In some embodiments, image analysis module 118 is configured to perform analysis on visual data acquired from imaging device 106. To achieve this, image analysis module 118 may include different components that perform different functions. For example, image analysis module 118 may include a background initialization manager 302 that is configured to compensate for any background elements present in the visual data. In some embodiments, a user may not be sitting in front of a plain background. For example, the background associated with the user and the field of view of imaging device 106 may not be static. Instead, the background may contain dynamic visual information associated with, for example, moving objects in the background. In some embodiments, background initialization manager 302 performs functions to characterize the background associated with the user. In some embodiments, this characterization may be performed in the user's presence. In other embodiments, this characterization may be performed in the user's absence. Background initialization manager 302 may include one or more visual reference points from the background as a part of any background initialization data that may be used for further processing. In some embodiments, characterizing the background associated with the user is performed by asking the user to sway from side to side, capturing the swaying motion of the user, and then using, for example, optical flow algorithms to determine any portions of the associated captured visual data that are non-stationary with respect to time. Non-stationary areas of the visual data are associated with the user swaying motion, versus the background not moving and associated with temporally static visual data. The temporally static visual data is used to characterize or initialize the background. In some embodiments, the user may be asked to sway to their left, sway to their right, and then return back to their center to complete the background characterization (initialization) process.

In some embodiments, image analysis module 118 may include a background tracking manager 304 that is configured to perform dynamic tracking on the background associated with the user in order to compensate for any dynamic components that may affect posture tracking of the user. For example, in the event that facial detection algorithms are included in the posture tracking process implemented by computing system 102, there may be other people with faces in the background. In some embodiments, a person may be looking over the shoulder of the user, for example, in response to the user wanting to share some information with the person. In such cases, the image recognition algorithm may recognize more than one face in the visual data and this might lead to errors in the posture tracking process. Background tracking manager 304 is configured to account for such errors and to prevent them from occurring. For example, a face in the background will be at a greater distance from imaging device 106 as compared to the face of user 104, as a result of which the latter will be recognized as a larger ellipse or blob by a facial detection algorithm as compared to the former. Background tracking manager is configured to track the largest ellipse or blob in a frame associated with the visual data as that is most likely the user's face while eliminating any other potentially distracting elements.

In some embodiments, background tracking manager 304 may be configured to compensate for any inadvertent movement in imaging device 106 relative to the position of user 104. For example, if user 104 is using a laptop and changes the tilt or orientation of the screen, the background data associated with user 104 may change. Similarly, the background data associated with user 104 may change if user 104 changes a position of the laptop (e.g., user 104 rotates the laptop, or moves the laptop towards or away from themselves). Background tracking manager 304 may be configured to account for such changes in the background by storing any key visual characteristics of the background and subsequently compensating accordingly. In some embodiments, after an initialization of the system is completed, user 104 is not required to re-initialize a predetermined posture.

Image analysis module 118 may also include a user initialization module 306 that is configured to initialize the system and store a predetermined posture using techniques described herein. In some embodiments, image analysis module 118 may include a posture detection manager 308 that may use image processing algorithms such as facial recognition or face detection to detect the current posture of user 104. In particular embodiments, image analysis module 118 may include a posture tracking manager 310 that is configured to track the current posture of user 104 in real time or substantially real time relative to a predetermined posture. In some embodiments, posture tracking manager 310 may use image processing algorithms such as facial recognition or face detection to track the current posture of user 104.

In some embodiments, image analysis module 118 may include a predetermined posture generator 312 that is configured to retrieve stored data associated with the predetermined posture and generate a rendition of the predetermined posture to be compared with the current posture of user 104. In some embodiments, image analysis module 118 may include a posture comparator 314 that compares the predetermined posture with the current posture of user 104 to compute any deviation in the current posture of user 104 from the predetermined posture. In some embodiments, a deviation in the current posture of user 104 from the predetermined posture is calculated by computing a pixel distance in the visual data between the predetermined posture and the current posture of user 104. In particular embodiments, the pixel distance—up, down, to the left, to the right, or any combination thereof—is a measure of the physical distance or physical deviation of the current posture of user 104 from the predetermined posture. In some embodiments, a percentage difference (increase or decrease) is used to determine any deviation in the current posture of user 104 from the predetermined posture in a direction towards or away from imaging device 106 respectively. If user 104 moves towards imaging device 106, the apparent size of user 104 as rendered by imaging device 106 increases relative to the predetermined posture, and vice versa. In some embodiments, the face of user 104 as detected using facial detection may be characterized as an elliptical shape in the visual data. The length and width (major and minor axes respectively) of this elliptical shape may be compared to a similar elliptical shape corresponding to the user's face associated with the predetermined posture. A relative increase or decrease in the number of pixels (for example, the area) of the elliptical shape corresponding to the face of user 104 relative to the elliptical shape corresponding to the predetermined posture may be used to determine whether user 104 has deviated from the predetermined posture while leaning towards or away from imaging device 106 respectively. If the deviation exceeds a certain predetermined threshold, an alert generator 316, included in image analysis module 118, is configured to generate one or more alerts that may include visual alerts, audible alerts, textual alerts, and so on.

In some embodiments, the predetermined threshold may be viewed as a system design parameter, and can be tuned to suit specific applications. For example, the predetermined threshold may be viewed as the number of pixels in the visual data by which the current posture of user 104 needs to deviate from the predetermined posture before the user is alerted about the deviation. In some embodiments, a relatively small threshold suggests a sensitive system that alerts user 104 for relatively small deviations in the current posture of user 104 from the predetermined posture. On the other hand, a relatively large threshold suggests a less sensitive or relatively relaxed system that responds only to larger deviations in the current posture of user 104 from the predetermined posture. In some embodiments, the predetermined threshold may be preset into posture analysis system 100. In particular embodiments, the predetermined threshold may be user-customizable.

In some embodiments, image recognition techniques may be implemented that preform recognition on a user's face to characterize the user's eyes, nose and lips to provide enhanced characterization of the current posture of user 104. Such techniques are especially useful in cases where, for example, the user might have rotated their head or if imaging device 106 is positioned to the side of user 104 or far below or far above user 104.

Figure 4:
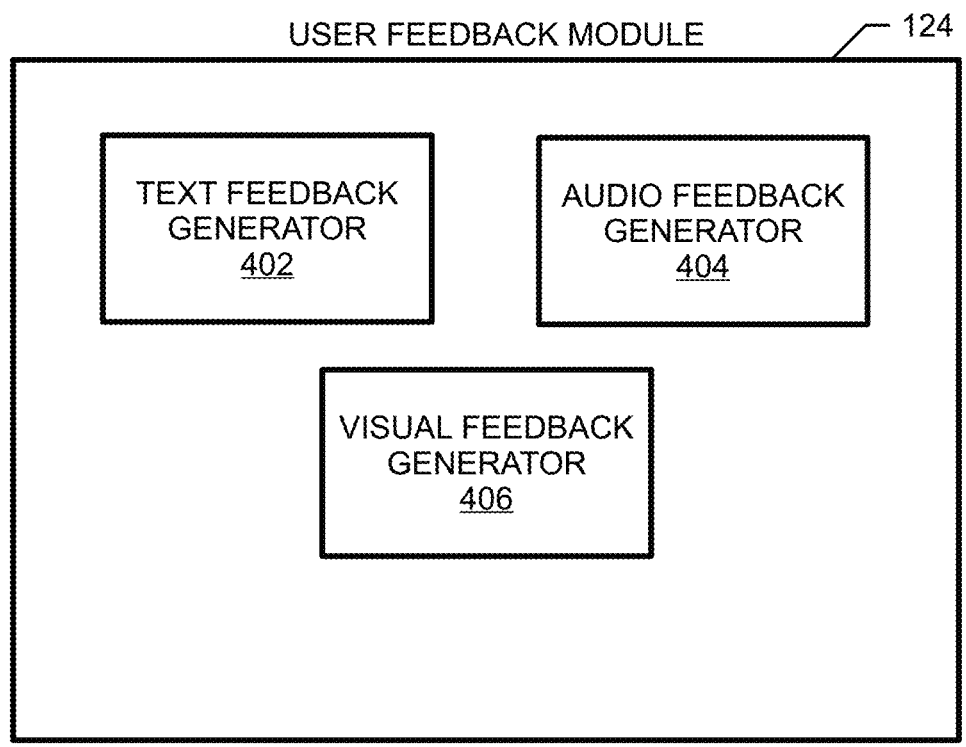
FIG. 4 is a block diagram depicting an embodiment of a user feedback module.

FIG. 4 is a block diagram depicting an embodiment of user feedback module 124 that is configured to provide feedback to a user of posture analysis system 100. In some embodiments, user feedback module 124 generates feedback for the user if the deviation associated with the user's current posture from the predetermined posture exceeds a certain threshold. User feedback module 124 may include a text feedback generator 402 that is configured to generate text messages that may be included, for example, in graphical image 110.

In some embodiments, user feedback module 124 may include an audio feedback generator 404 that is configured to generate audio signals that may be played back on, for example, a speaker associated with computing system 102 or display device 108 (not shown). In some embodiments, user feedback module 124 may include a visual feedback generator 406 that is configured to generate visual feedback signals to user 104 that inform user 104 about any deviation in the current posture of user 104 from the predetermined posture. In some embodiments, the visual feedback signals may be provided to user 104 via graphical image 110.

Figure 5A:
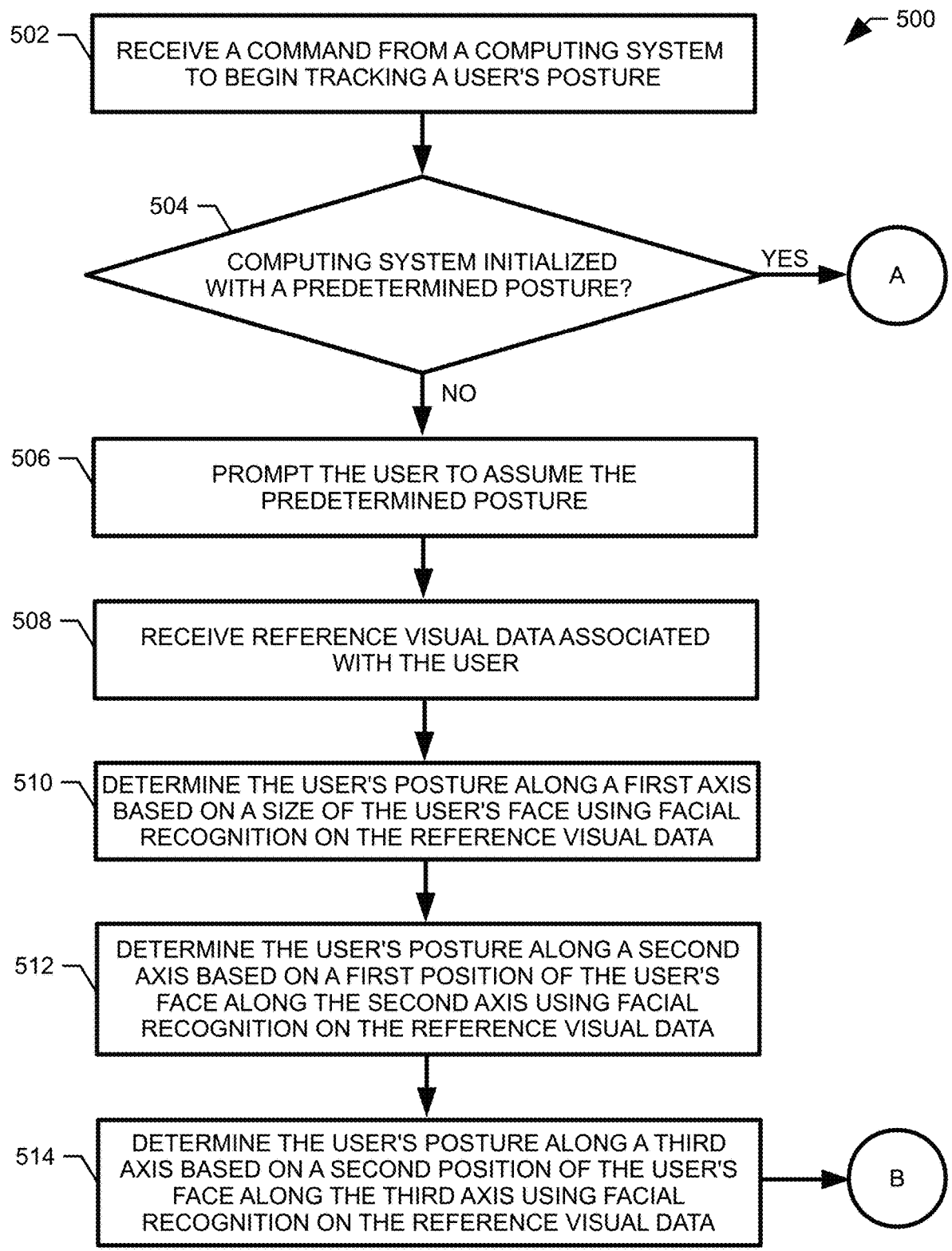
FIGS. 5A-5E represent a flow diagram depicting an embodiment of a method to track and correct a user's posture in substantially real time.

FIG. 5A represents a flow diagram depicting an embodiment of a method 500 to track and correct a user's posture in substantially real time. At 502, the method receives a command from a computing system (such as computing system 102) to begin tracking a user's posture. At 504, the method determines whether the computing system is initialized with a predetermined posture. If the computing system is initialized with a predetermined posture the method goes to A, with a continued description provided herein. If, at 504, the computing system is not initialized with a predetermined posture, the method goes to 506, where the user is prompted to assume the predetermined posture. In some embodiments, the user may be prompted to assume the predetermined posture by computing system 102 via any combination of text and graphics rendered on graphical image 110 as displayed on display device 108. In some embodiments, the user may be assisted in assuming the predetermined posture by offering, for example, text prompts to the user on graphic element 114 such as "sit up straight," or "make sure your shoulders are not slouching," and so on. At 508, the method receives reference visual data associated with the user, where the reference visual data is associated with the user assuming the predetermined posture. In some embodiments, the reference visual data may be received from imaging device 106. At 510, the method determines the user's posture along a first axis based on a size of the user's face using, for example, facial detection on the reference visual data. In some embodiments, the first axis is substantially parallel to the optical axis of imaging device 106 which, in turn, may be substantially orthogonal to the plane of display device 108. In particular embodiments, a user may move their body along the first axis. The motion of the user along the first axis causes the size of the user's face in the visual data to change. When the user moves closer to imaging device 106 the user's face appears larger in the visual data and vice versa. When the user assumes the predetermined posture, the size of the user's face is associated with the predetermined posture that corresponds to a specific distance from imaging device 106 along the optical axis of imaging device 106; this is the basis used for step 510.

At step 512, the method determines the user's posture along a second axis based on a first position of the user's face along the second axis using, for example, facial detection on the reference visual data. In some embodiments, this second axis may be substantially orthogonal to the optical axis of imaging device 106 and substantially parallel to a plane associated with display device 108. At step 514, the method determines the user's posture along a third axis based on a first position of the user's face along the third axis using, for example, facial detection on the reference visual data. In some embodiments, this third axis may be substantially orthogonal to the optical axis of imaging device 106, substantially parallel to the plane associated with display device 108, and substantially orthogonal to the second axis. Steps 512 and 514 aim to characterize the position of the user's face in two dimensions in a plane substantially parallel to the plane associated with display device 108. In some embodiments, the combination of the first axis, the second axis and the third axis forms a three-dimensional, substantially orthogonal coordinate system. Steps 510, 512 and 514 together may be used to provide a three-dimensional spatial characterization (using the first axis, second axis, and third axis) of the position of the user's face, and hence the user's posture, based on the three-dimensional, substantially orthogonal coordinate system. This feature allows posture analysis system 100 to perform three-dimensional tracking of a current posture associated with the user. In some embodiments, the motion of the user's face along each of the three axes may be any combination of translation and rotational motion. The method then goes to B, with a continued description provided subsequently.

Figure 5B:
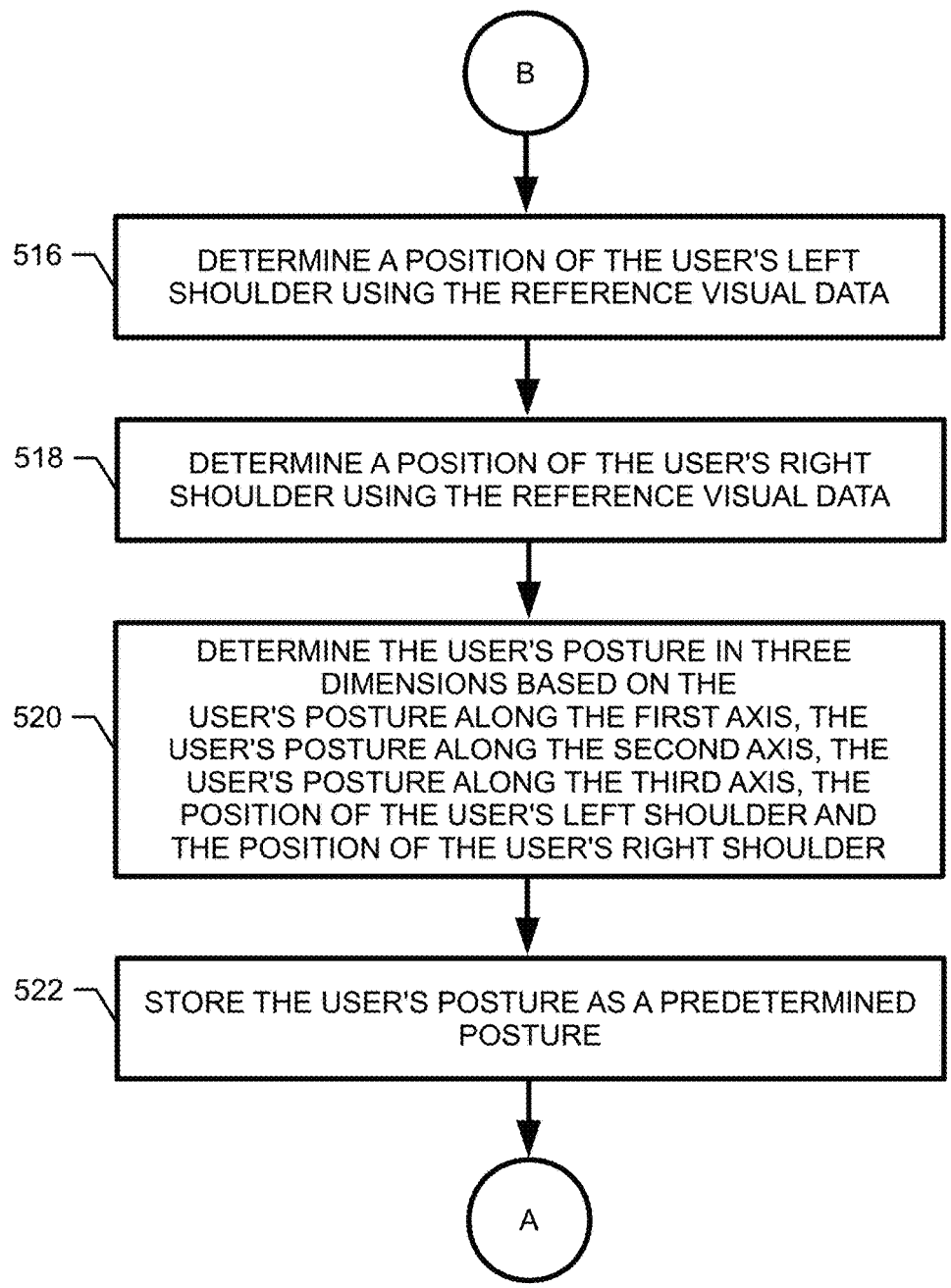

FIG. 5B is a continued description of the method 500. Starting at B, the method 500 goes on to include spatial data associated with the user's shoulders to augment the three-dimensional characterization of the user's posture based on facial detection steps 510 through 514. At 516, the method determines a position of the user's left shoulder using the reference visual data. At 518, the method determines a position of the user's left shoulder using the reference visual data. In some embodiments, steps 516 and 518 may be accomplished by the user swaying from side to side in front of imaging device 106 so that posture analysis system 100 can determine the position of the user's left shoulder and the position of the user's right shoulder from the visual data. In other embodiments, steps 516 and 518 may be accomplished by having the user wiggle their shoulders in front of imaging device 106.

In other embodiments, steps 516 and 518 may be accomplished by having the user stroke their left shoulder and right shoulder respectively, with image detection techniques being used to determine a position of the user's left shoulder and a position of the user's right shoulder. In particular embodiments, an area below the detected face of the user may be divided into a left portion and a right portion, with a search being performed in each of the left portion and the right portion to detect the user's left shoulder and right shoulder respectively.

At 520, the method determines the user's posture in three dimensions based on the user's posture along the first axis, the user's posture along the second axis, the user's posture along the third axis, the position of the user's left shoulder and the position of the user's right shoulder. In some embodiments, data associated with modeling the user's posture in three dimensions includes using an ellipse or polygon as an output of the facial detection system that is used to model the user's face. The centroid of the ellipse or polygon is determined, and the coordinates of the centroid of the ellipse or polygon relative to a two-dimensional coordinate system comprising the second axis and the third axis is stored along with the length, width and area of the ellipse or polygon. The length, width and area of the ellipse or polygon give a measure of the motion of the user relative to the first optical axis. The measurements of the coordinates of the centroid of the ellipse or polygon and the length, width and area of the ellipse or polygon provide a three-dimensional characterization or modeling of the posture data.

In some embodiments, at 520, the upper left location of each shoulder relative to a coordinate system formed by the second axis and the third axis is used to model posture data associated with the user's shoulders. Next, at 522, the method stores the user's posture as a predetermined posture. The method continues to A, with a continued description provided subsequently.

Figure 5C:
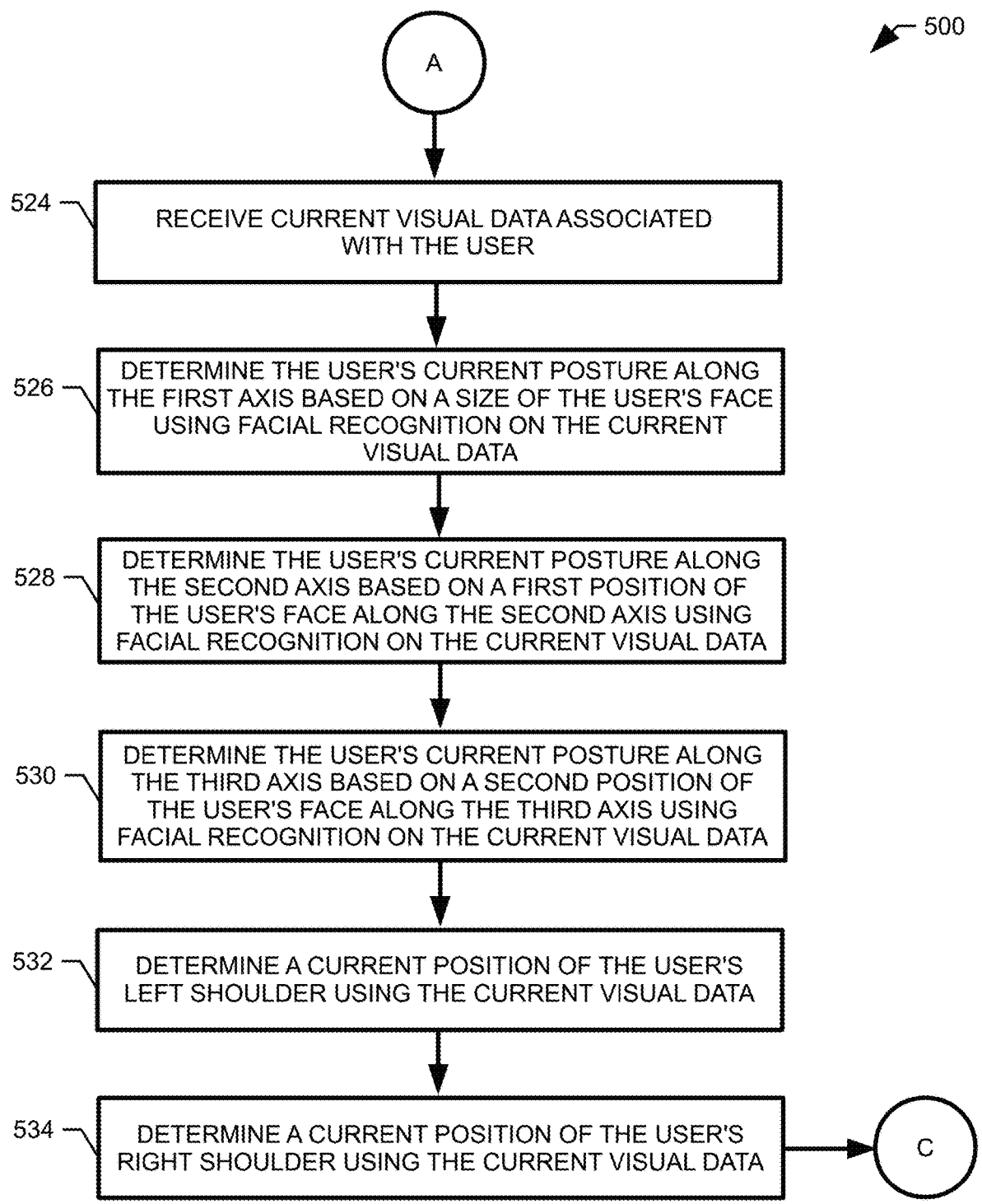

FIG. 5C is a continued description of the method 500. While steps 506 through 522 described the generation of the predetermined posture (that can also be referred to as system calibration), subsequent steps describe the operation of the system with respect to posture monitoring and tracking for a given user associated with a predetermined posture.

Starting at A, the method continues to 524, where the computing system receives current visual data associated with the user. "Current visual data" is used to refer to visual data associated with user posture monitoring and tracking. In some embodiments, the current visual data may be received from imaging device 106. At 526, the method determines the user's current posture along the first axis based on a size of the user's face using facial detection on the current visual data. This process is similar to step 510. At 528, the method determines the user's current posture along the second axis based on a first position of the user's face along the second axis using facial detection on the current visual data. This process is similar to step 512. At 530, the method determines the user's current posture along the third axis based on a second position of the user's face along the third axis using facial detection on the current visual data. This process is similar to step 514. Next, at 532, the method determines a current position of the user's left shoulder using the current visual data. This process is similar to step 516. At 534, the method determines a current position of the user's right shoulder using the current visual data. This process is similar to step 518. The method then proceeds to C, with a continued description provided subsequently.

Figure 5D:
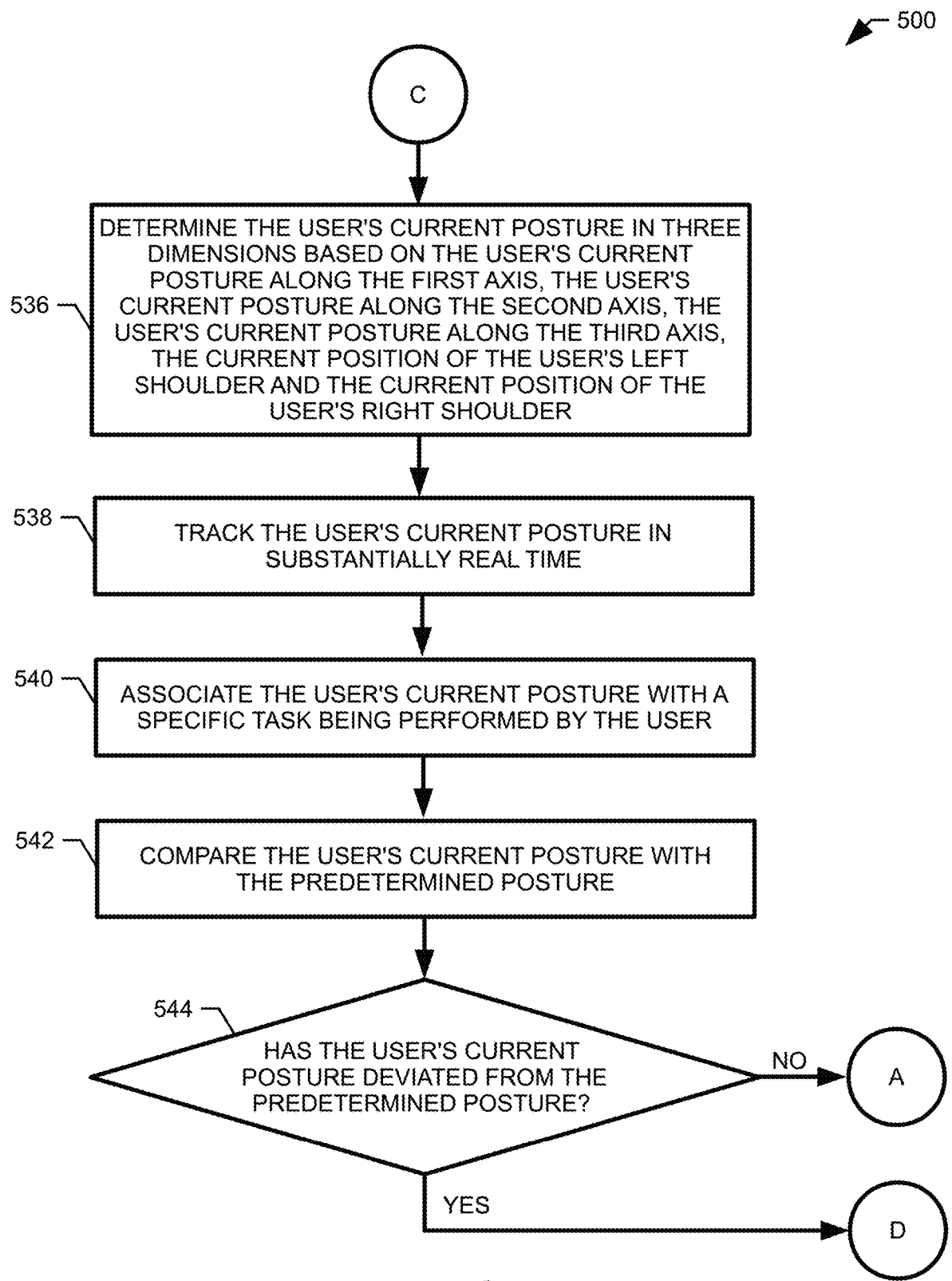

FIG. 5D is a continued description of the method 500. At 536, the method determines the user's current posture in three dimensions based on the user's current posture along the first axis, the user's current posture along the second axis, the user's current posture along the third axis, the current position of the user's left shoulder and the current position of the user's right shoulder. This process is similar to step 520. Next, at 538, the method tracks the user's current posture in substantially real time. In some embodiments, tracking the user's current posture is performed at a rate that is similar to the frame rate of imaging device 106, for example, 30 frames per second. Other embodiments may implement faster or slower tracking rates depending on the specific system or user requirements or available system resources. For example, frame rates may range from 5 frames per second to 2000 frames per second. At 540, the method associates the user's current posture with a specific task being performed by the user (e.g., a task being performed on the computing system). This association of the user's current posture with a particular task may allow posture analysis system 100 to potentially identify bad posture habits associated with performing the particular task. For example, a user may slouch while using a word processor, crane their neck while reading an email, or shrug their shoulders when watching a video. All these associations of bad posture habits can be associated with a specific task being performed by the user and then provided to the user at a later time to allow them to take corrective steps for assuming a healthy posture.

At 542, the method compares the user's current posture with the predetermined posture. At 544, the method determines whether the user's current posture has deviated from the predetermined posture. In some embodiments, steps 542 and 544 may be accomplished by posture comparator 314. If the user's posture has not deviated from the predetermined posture the method returns to A. If the user's posture has deviated from the predetermined posture the method continues to D, with a continued description provided subsequently.

Figure 5E:
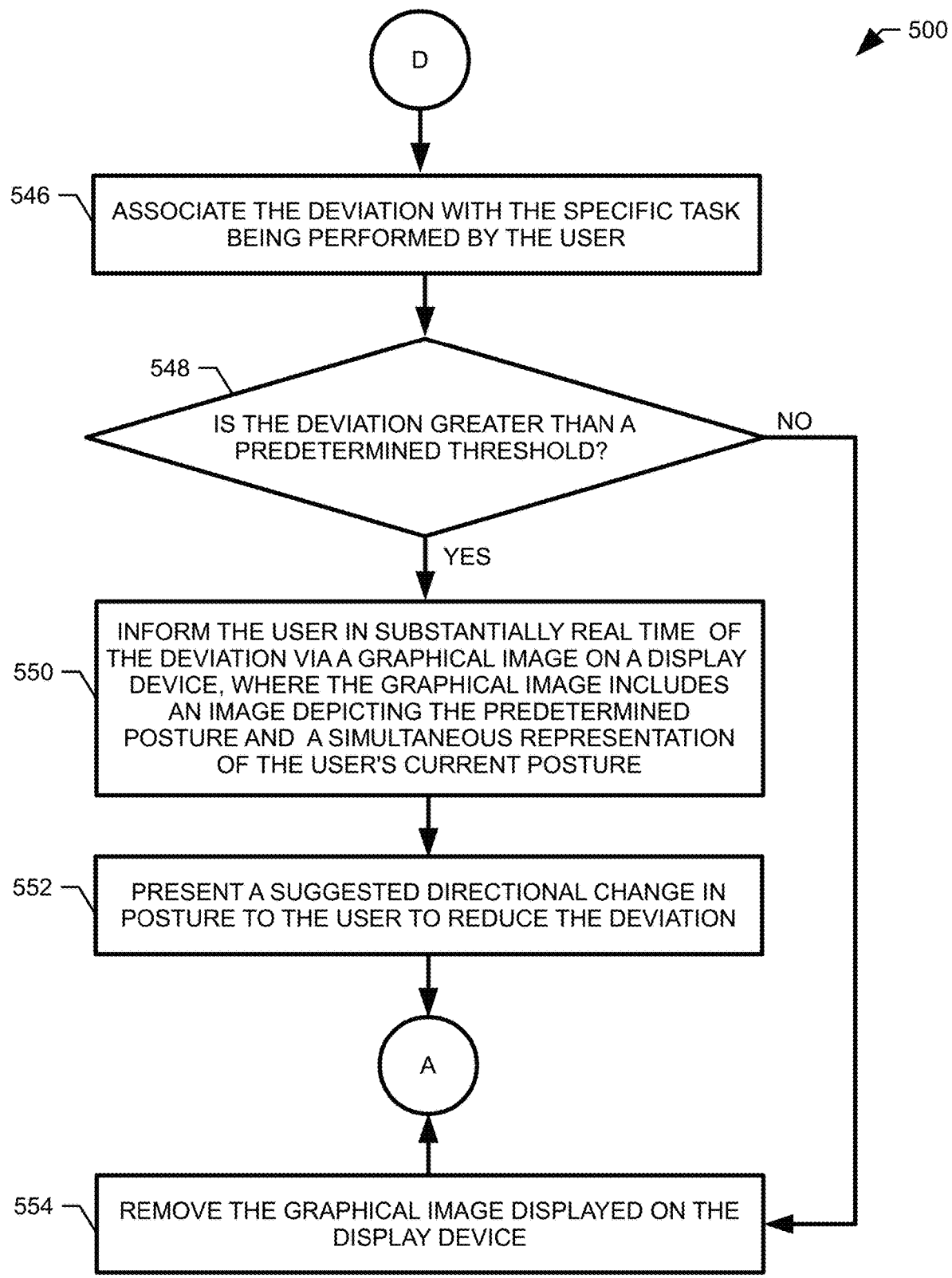

FIG. 5E is a continued description the method 500. At 546, the method associates the deviation with the specific task being performed by the user. While step 540 associates the user's current posture with a specific task being performed by the user on the computing system, step 546 associates the deviation associated with the user's current posture from the predetermined posture with the specific task being performed by the user. This allows posture analysis system 100 to characterize bad posture habits associated with a user in relation to a specific task being performed by the user. Next, at 548, the method determines whether the deviation is greater than a predetermined threshold. In some embodiments, each of the first axis, the second axis, and the third axis is monitored to determine a deviation in the user's current posture from the predetermined posture. A deviation of the user's current posture from the predetermined posture along one or more axis by over a threshold associated with that axis is sufficient for method 500 to trigger an alert or suggestion to the user. In one example, the thresholds associated with the axes are:

- Approximately 32 pixels along the second axis in either direction, with the second axis being substantially parallel to a horizon associated with the user.
- Approximately 18 pixels along the third axis in either direction, with the third axis being substantially orthogonal to the second axis.
- An approximately 10% to 30% deviation in either direction in the size (length, width and area) of an ellipse or polygon associated with the user's face along the third axis, with the third axis being substantially orthogonal to the plane formed by the second axis and the third axis.

In some embodiments, an alert may be generated for a deviation of the user along the second axis by 32 pixels or more. However a corrective motion of approximately 15 pixels and the user assuming the associated posture for a predetermined amount of time may cause posture detection system 100 to remove the alert.

If the deviation is greater than the predetermined threshold then the method continues to 550, where the method informs the user in substantially real time of the deviation via a graphical image (for example, graphical image 110) on a display device (for example, display device 108). The graphical image includes an image depicting the predetermined posture and a simultaneous representation of the user's current posture. In some embodiments, the predetermined posture may be depicted using a line rendition. In particular embodiments, the user's current posture may be represented by an ellipse corresponding to the current position of the user's face as determined by facial detection algorithms running on the computing system. In some embodiments, the representation of the predetermined posture or the user's current posture may be customizable by the user. Details about the presentation and operation of the graphical image are presented herein.

In some embodiments, method 500 may also include any combination of averaging, smoothing, or probabilistic functions that prevent the system from triggering false alarms due to any measurement errors associated with posture analysis system 100. For example, a measurement error that shows a user posture "jumping" by too many pixels may be filtered (or ignored) by these functions as they are associated with false alarms and measurement uncertainties rather than any realistic motion by the user. As used herein, the term "filtering" includes system operations such as avoiding pixels or other items, ignoring pixels or other items, accounting for pixels or other items, rejecting pixels or other items, disregarding pixels or other items, and so on. In some embodiments, the goal of the filtering operation is to avoid taking into consideration unrealistic jumps in the user's current posture as determined from the visual data due to measurement errors associated with the system. Including the filtering operation as a part of the functionality of posture tracking system 100 enhances the operation and accuracy of posture analysis system 100 by, for example, eliminating or reducing the probability of any occurrences of false alarms or false positioning associated with deviations in the current user's posture.

In some embodiments, posture analysis system 100 may introduce a time delay between step 548 and step 550. In particular embodiments, the time delay may be approximately ⅓ seconds, or 320-370 milliseconds. Introducing the time delay is done to account for a user swaying back and forth about a mean position that is the predetermined posture, a process considered acceptable for healthy posture. Without the built-in lag, posture analysis system 100 may exhibit an overly sensitive response to user inputs. In alternate embodiments, any value may be used as a time lag in posture analysis system 100.

At 552, the method presents a suggested directional change in posture to the user to reduce the deviation. Essentially, this step is a posture correction suggestion step. In some embodiments, suggestions may be provided by any combination of text messages included graphical symbols such as arrows, or any other similar symbols included in, for example, graphical image 110. Step 552 may also include audio feedback to the user in the form of coded messages (e.g., beeps) or explicit verbal feedback (via, for example, prerecorded voice messages). The method then goes back to A.

Returning to 548, if the method determines that the deviation is not greater than the predetermined threshold then the method goes to 554, where the graphical image displayed on the displayed device, if present, is removed, and the method returns back to A.

Figure 6:
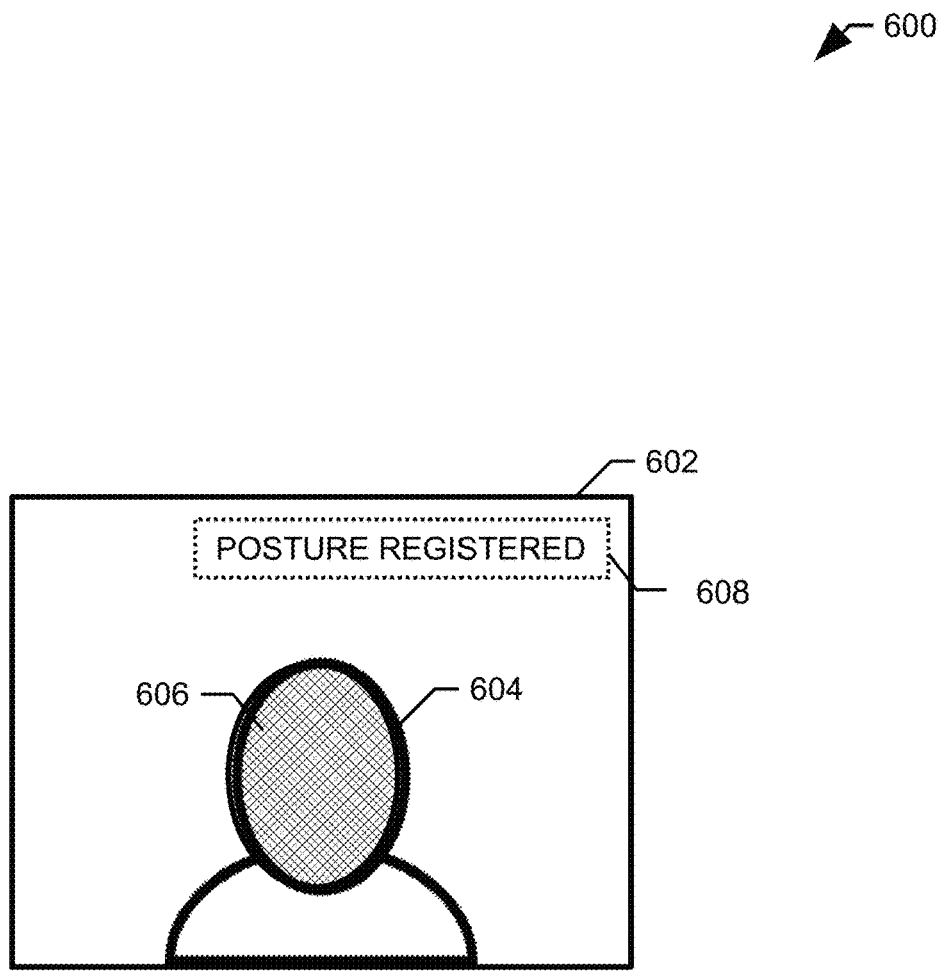
FIG. 6 is a schematic diagram depicting an embodiment of a posture analysis system interface that shows a registration of a predetermined posture.

FIG. 6 is a schematic diagram depicting an embodiment of a posture analysis system interface 600 that shows a registration of a predetermined posture. In some embodiments, the process of posture registration is performed using a graphical image 602 displayed on, for example, imaging device 108. In some embodiments, graphical image 602 may be identical to graphical image 110.

In some embodiments, when the user assumes a predetermined posture after being prompted (for example, in step 506 of method 500), the user may press a certain key on the keyboard or click a graphical button displayed on display device 108 using their mouse or use a predetermined or pre-established gesture that may be captured by imaging device 106 and recognized by a computer vision system to confirm that they have assumed the predetermined posture. In response to the confirmation, computing system 102 receives visual data, processes the visual data to extract the predetermined posture, and stores the predetermined posture. In some embodiments, the user may be given a time frame (e.g., 5 seconds or 10 seconds) to assume and maintain the predetermined posture. During this time frame, the computing system receives visual data, processes the visual data to extract the predetermined posture, and stores the predetermined posture.

In some embodiments, computing system 102 may render the predetermined posture as a line drawing 604 on graphical image 602, along with an ellipse 606 that provides a location of the user's face, where ellipse 606 is substantially congruent to and substantially identically located with the face portion of line drawing 604. In some embodiments, ellipse 606 may be replaced by other graphic symbols that may be user selectable, such as cartoon characters, caricatures, renditions of animals, flowers, other kinds of avatars, and the like. In some embodiments, upon successful registration of the predetermined posture, computing system 102 may present a text message 608 to the user confirming that the posture has been registered. For example, as depicted in FIG. 6, text message 608 may read "Posture Registered." The posture analysis system 100 is now configured to begin tracking the user's posture in substantially real time and informing the user of any deviations from the predetermined posture in substantially real time.

Figure 7:
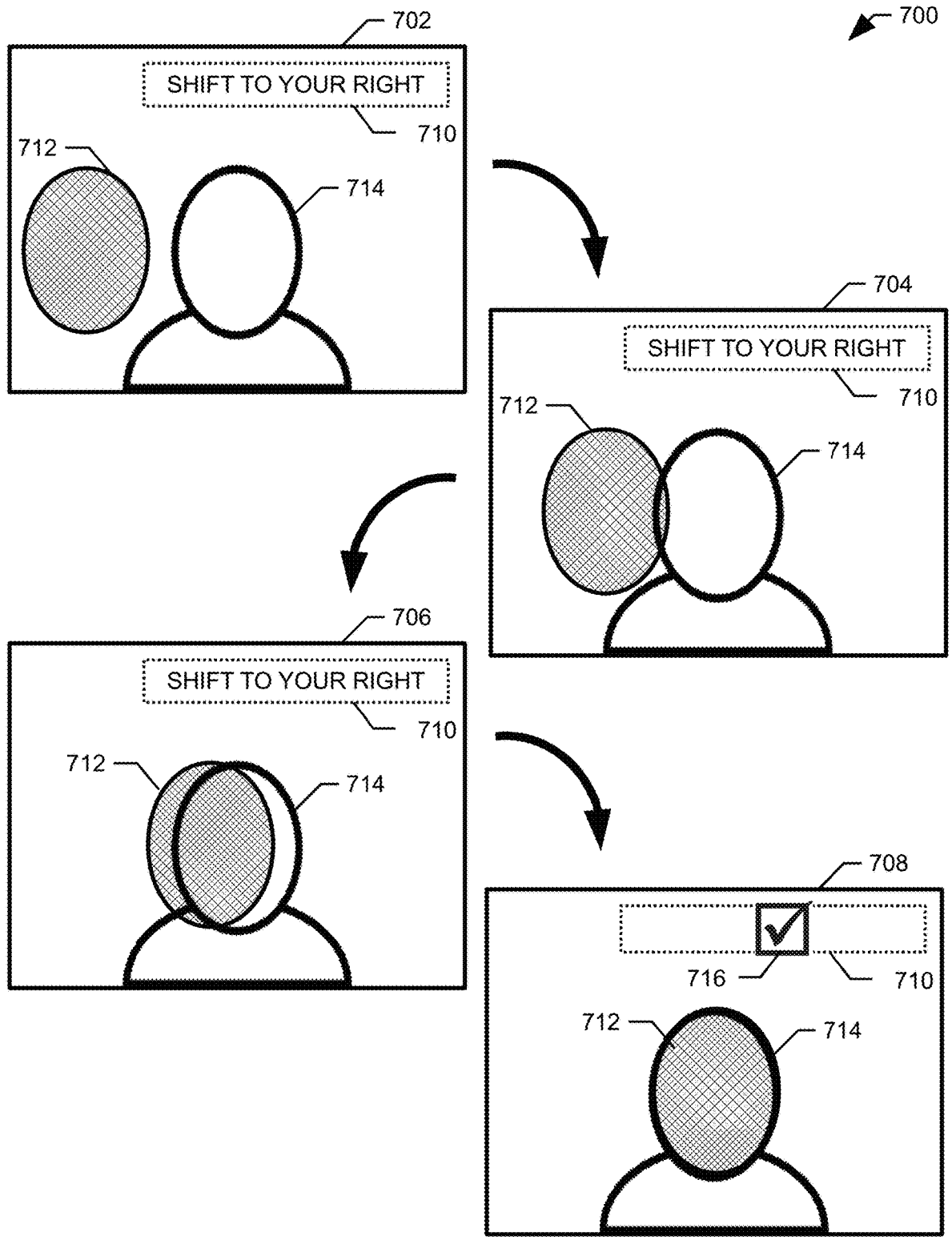
FIG. 7 is a schematic diagram depicting an embodiment of an interactive posture correction sequence.

FIG. 7 is a schematic diagram depicting an embodiment of an interactive posture correction sequence 700. In some embodiments, a user's current posture may deviate from the predetermined posture. If the computing system determines that this deviation is greater than a predetermined threshold, computing system 102 may alert user 104 by presenting relevant information on a graphical image 702 that includes a line rendition 714 of the predetermined posture. In some embodiments, graphical image 702 may also depict an ellipse 712 corresponding to a three-dimensional position of the user's face relative to the reference posture as represented by line rendition 714. In this case, the deviation of the user's current posture from the predetermined posture is shown to be to the left of line rendition 714. Graphical image 702 may also include textual information such as a text message 710 that prompts the user to shift their posture in a particular direction to reduce or eliminate the deviation. For example, FIG. 7 shows text message 710 displaying the prompt "shift to your right," to allow the user to compensate for the deviation to the left. In addition to text message 710, audio feedback via encoded audio signals or explicit voice recordings may be provided to the user.

FIG. 7 depicts a sequence of events that occurs as displayed to a user, starting with graphical image 702, as the user corrects their posture. In response to the prompt on text message 710, as the user starts to shift to their right, correction sequence 700 may replace graphical image 702 by a graphical image 704 that includes line rendition 714. As the user responds to text message 710 and moves to their right, the rendition of the user's face also moves to the right, as depicted by ellipse 712. In graphical image 704, ellipse 712 is shifted to the right as compared to the position of ellipse 712 in graphical image 702, corresponding to the user's response to the prompt on text message 710. Since there still is a deviation in the user's posture compared to the predetermined posture text message 710 in graphical image 704 still includes text message 710 "shift to your right." In addition to text message 710, audio feedback via encoded audio signals or explicit voice recordings may be provided to the user.

As the user moves further to their right in response to the prompt on text message 710, correction sequence 700 replaces graphical image 704 by a graphical image 706 that includes line rendition 714, as in graphical image 702 and graphical image 704. As the user responds to text message 710 and moves to their right, the rendition of the user's face also moves to the right, as depicted by ellipse 712. In graphical image 706, ellipse 712 is shifted to the right as compared to the position of ellipse 712 in graphical image 704, corresponding to the user's response to the prompt on text message 710. While the user is closer to the predetermined posture in graphical image 706 as compared to graphical image 704, there still is a deviation in the user's posture compared to the predetermined posture; hence text message 710 in graphical image 706 still reads "shift to your right." In addition to text message 710, audio feedback via encoded audio signals or explicit voice recordings may be provided to the user.

Once the user assumes the predetermined posture as shown by a graphical image 708, a rendition of the user's face via ellipse 712 now coincides with the representation of the user's face on line rendition 714 that depicts the predetermined posture, as depicted on graphical image 708. Since the user has now assumed the predetermined posture and corrected for the deviation, text message 710 in graphical image 708 may now depict a check mark 716 that provides a confirmation to the user that they have assumed the predetermined posture. In some embodiments, check mark 716 may be replaced with a congratulatory message or some other congratulatory graphic that may be displayed while posture analysis system may also provide audio feedback to the user via encoded audio signals or explicit voice recordings.

In some embodiments, posture analysis system 100 may remove the graphical image, such as graphical image 708, from display device 108 after a certain time interval once the user assumes and maintains the predetermined posture. In some embodiments, processing system 102 may process visual data at a lower frame rate once the user has assumed the predetermined posture with graphical image 708 removed from display device 108. This is done to reduce any computing resource utilization by posture analysis system 100 on computing system 102 when the user maintains the predetermined posture. When the user deviates from the predetermined posture and needs interactive feedback, processing system 102 may process visual data at a higher frame rate to provide substantially real time updates to the user via a graphical image such as graphical image 702.

Figure 8:
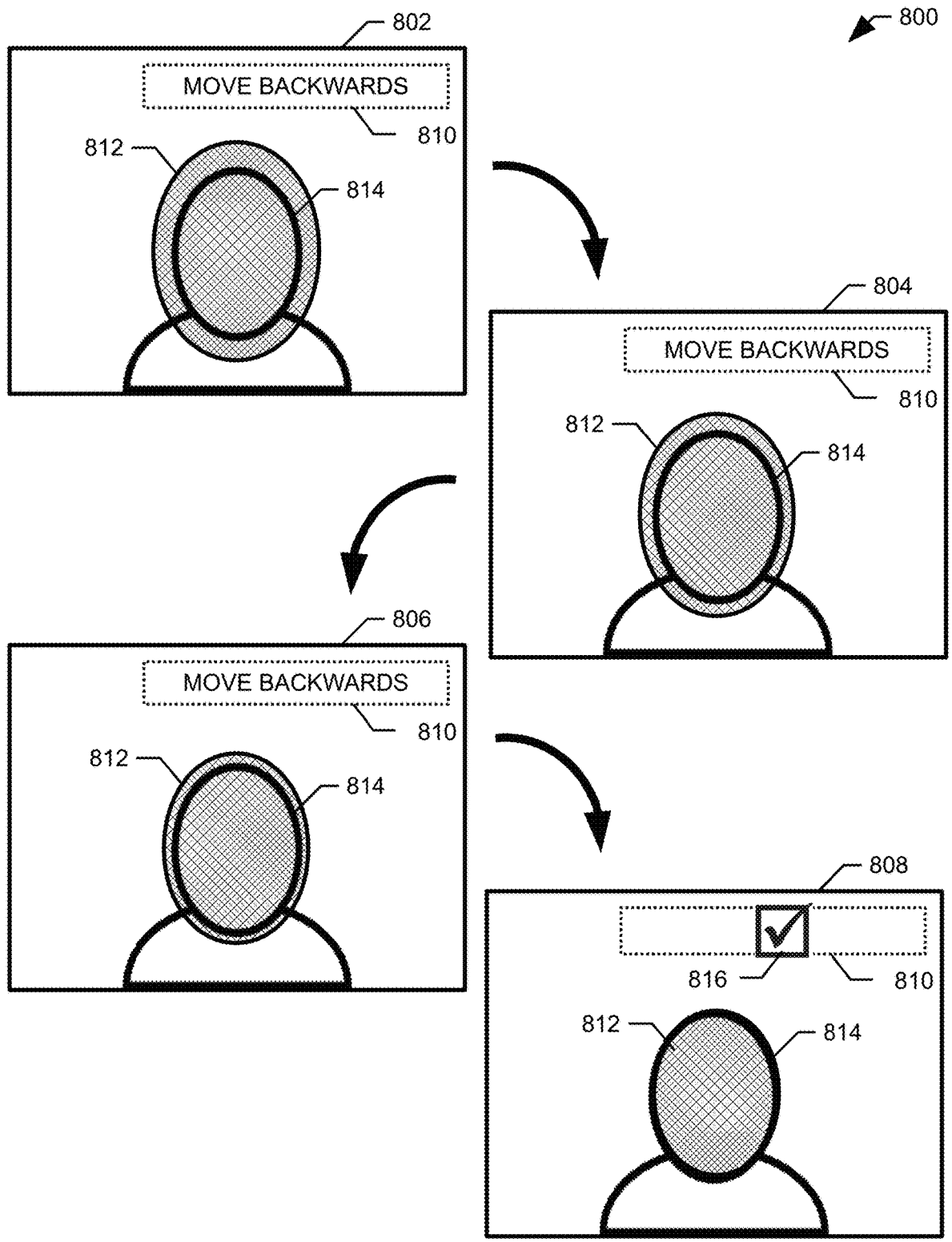
FIG. 8 is a schematic diagram depicting another embodiment of an interactive posture correction sequence.

FIG. 8 is a schematic diagram depicting another embodiment of an interactive posture correction sequence 800. In some embodiments, a user's current posture may deviate from the predetermined posture. If the computing system determines that this deviation is greater than a predetermined threshold, computing system 102 may alert user 104 by presenting relevant information on a graphical image 802 that includes a line rendition 814 of the predetermined posture. In some embodiments, graphical image 802 may also depict an ellipse 812 corresponding to a three-dimensional position of the user's face relative to the reference posture. In this case, the deviation in the user's current posture from the predetermined posture is in a direction towards imaging device 106 (i.e., the user's current position is too close to imaging device 106 relative to the predetermined posture), resulting in larger facial dimensions as determined by a facial detection algorithm running on computing system 102. Graphical image 802 may also include textual information such as a text message 810 that prompts the user to shift their posture in a particular direction to reduce or eliminate the deviation. For example, FIG. 8 shows text message 810 displaying the prompt "move backwards." In addition to text message 810, audio feedback via encoded audio signals or explicit voice recordings may be provided to the user.

FIG. 8 depicts a sequence of events that occurs as displayed to a user starting with graphical image 802 as the user corrects their posture. In response to the prompt on text message 810, as the user starts to move backwards, correction sequence 800 may replace graphical image 802 with a graphical image 804 that includes line rendition 814. As the user responds to text message 810 and moves backwards, the size of ellipse 812 in graphical image 814 associated with the rendition of the user's face reduces and beings to approach the size of the face in the predetermined posture as represented by line rendition 814. (The size of the user's face is depicted by ellipse 812.) Since there still is a deviation in the user's posture compared to the predetermined posture, text message 810 in graphical image 804 still reads "move backwards." In addition to text message 810, audio feedback via encoded audio signals or explicit voice recordings may be provided to the user.

As the user continues to move backwards in response to the prompt on text message 810, correction sequence 800 replaces graphical image 804 by a graphical image 806 that includes line rendition 814, as in graphical image 802 and graphical image 804. As the user responds to text message 810 and moves backwards, the rendition of the user's face (i.e., the size of ellipse 812 used to depict the user's face in graphical image 806) also reduces in size. While the user is closer to the predetermined posture, there still is a deviation in the user's posture compared to the predetermined posture; hence text message 810 in graphical image 806 still reads "move backwards." In addition to text message 810, audio feedback via encoded audio signals or explicit voice recordings may be provided to the user.

Once the user assumes the predetermined posture to reach a final state 808, a rendition of the user's face via ellipse 812 now coincides with the representation of the user's face on line rendition 814 that depicts the predetermined posture, as depicted on graphical image 808. Since the user has now assumed the predetermined posture and corrected for the deviation, text message 810 in graphical image 808 may now depict a check mark 816 that provides a confirmation to the user that they have assumed the predetermined posture. In some embodiments, check mark 816 may be replaced with a congratulatory message or some other congratulatory graphic that may be displayed while posture analysis system may also provide audio feedback to the user via encoded audio signals or explicit voice recordings.

In some embodiments, feedback provided to the user to correct their posture may include shading at least one portion of graphical image 110 based on the deviation of the user's current posture from the predetermined posture. In particular embodiments, the term "shading" is used to signify operations such as reducing the luminosity of at least one portion of graphical image 110, changing the color of at least one portion of graphical image 110, and the like. In some embodiments, the shading may be graduated to transition (or fade) into the remaining portion of graphical image 110 that is not shaded. In other embodiments, there may be a high contrast between a shaded portion and an unshaded portion of graphical image 110. In particular embodiments, the shading may be transparent. In other embodiments, the shading may be opaque. In still other embodiments, the shading may be translucent.

In some embodiments, a portion of graphical image in a direction corresponding to the deviation may be shaded. For example, if the user deviates to their right, a right-hand portion of graphical image 110 may be shaded. If the user deviates above the predetermined posture, a top portion of graphical image 110 may be shaded. Forwards or backwards deviations may be denoted by introducing vignetting (i.e., lightening or darkening a periphery) of graphical display 110. Combinations of deviations along separate axes (e.g., up and left) may be denoted by shading, for example a top left corner (to include a left-hand edge and a top edge) of graphical display 110, and so on.

In some embodiments, the concept of shading may be extended to display device 108, where at least one portion of display device 108 is shaded based on a deviation of the user's current posture from the predetermined posture. The methods and techniques described above for shading graphical display 110 may also be used on display device 108. In a particular embodiment, one or more edges associated with display device 108 may be shaded depending on the direction of the deviation. For example, if the deviation is to the right of the user, a right-hand edge or a right-hand portion of display device 108 may be shaded to alert the user of the deviation and the associated direction. Or, if the deviation is to the left and down, a lower left-hand corner (to include a bottom edge and a left-hand edge) of display device 108 may be shaded.

In some embodiments, posture analysis system 100 may remove the graphical image such as graphical image 110 or graphical image 808 from display device 108 after a certain time interval once the user assumes and maintains the predetermined posture. In some embodiments, processing system 102 may process visual data at a lower frame rate once the user has assumed the predetermined posture with graphical image 110 removed from display device 108. This is done to reduce any computing resource utilization by posture analysis system 100 on computing system 102 when the user maintains the predetermined posture. When the user deviates from the predetermined posture and needs interactive feedback, processing system 102 may process visual data at a higher frame rate to provide substantially real time updates to the user via graphical image 802.

In some embodiments, the user's shoulders will be indicated both with the predetermined posture and the current user posture with a box and a colorful icon which should be in the box, or by using any other graphical, textual or audible feedback method. In some instances, the user's head might move forward but the shoulders stay in place. This motion implies that the user is craning their head forward. Or, the user's shoulders may be moving up left and/or right. This posture suggests that the user may be shrugging. As another example, the user's shoulders may be rendered as falling down left and/or right. This is associated with the possibility of a deflating-kind of posture. In some embodiments, user messages presented in response to, for example, the user shrugging may be similar to "You are shrugging left" or "You are shrugging right," depending on which direction the user is shrugging. The corresponding visual depiction could include a close-up of a shoulder, neck, part of head that shows a shoulder out of place and a downward arrow suggesting that the user lower their shoulder.

FIGS. 7 and 8 characterize the three-dimensional operational ability of posture analysis system 100. The individual scenarios indicated in FIGS. 7 and 8 are example representations provided for purposes of explanation. In some embodiments, a user posture may be a combination of the scenarios depicted in FIGS. 7 and 8, which would constitute a full three-dimensional representation. Being able to dynamically suggest posture corrections allows posture analysis system 100 to detect and suggest corrections for unhealthy postures such as slouching, shrugging, craning of the neck, and so on by a user. Including the position of the user's shoulders provides increased capability to the system in some conditions such as craning of the neck, while also allowing posture analysis system 100 to characterize the position of the user's head in relation to the user's shoulders. In particular embodiments, the position of the user's face is sufficient to characterize the user's current posture and provide associated posture correction feedback.

In some embodiments, posture analysis system 100 can also provide additional visual cues that help the user correct their posture. For example, suppose the deviation in the current posture of the user from the predetermined posture is to the left. Posture analysis system may shade a portion of the left-hand side of graphic element 114 to provide a visual cue to the user to shift to the right. Sections of graphic element 114 may be shaded in a similar fashion, respectively corresponding to deviations in the user's posture from the predetermined posture.

In some embodiments, posture analysis system 100 can also provide suggestions other than posture corrections. These suggestions may be aimed at, for example, reducing user fatigue. For instance, posture analysis system 100 may detect that a user may have assumed the predetermined posture without moving for a particular period of time. Since assuming a particular posture for long periods of time without moving is also unhealthy, posture analysis system 100 can provide a user with prompts, suggesting that they get up, take a break, shift their position, or stretch.

The system may also include blink detection. A facial detection algorithm may include an ability to detect and monitor a user's eyes. If posture analysis system 100 determines that the user has not blinked for a period of time, posture analysis system 100 can prompt the user accordingly, thus aiming to reduce eye fatigue.

To reduce resource utilization by posture analysis system 100 on computing system 102, posture analysis system 100 may use a relatively high frame rate of 30 frames per second of visual data when a deviation is detected in the user's current posture as compared to the predetermined posture, such as during the time when graphical image 110 is being displayed to the user along with the associated feedback. When the user has assumed the predetermined posture after correcting for the deviation, graphical image 110 may be removed and the processing frame rate may be reduced.

In some embodiments posture analysis system 100 may include a lag of approximately ⅓ seconds, or 320-370 milliseconds to account for a user swaying back and forth about a mean position that is the predetermined posture, a process considered acceptable and encouraged for maintaining healthy posture. Without the built-in lag, posture analysis system 100 may exhibit an overly sensitive response to user inputs. In alternate embodiments, any value may be used as a time lag in posture analysis system 100.

In some embodiments, a user may be able to configure the line representation associated with graphical image 110, and may have access to customized avatars to allow them to customize the graphical image to their taste. In some embodiments, the colors associated with graphical image 110 may be automatically configured by posture analysis system 100 in accordance with importance. For example, an initial deviation in the user's posture may be rendered on graphical image 110 in subtle colors (for example, green). However, these colors may be replaced by stronger, more saturated colors (e.g., red or orange) if the user does not pay attention to the posture correction alerts for a certain period of time. As another example, yellow may be used to denote an initial deviation in the user's posture relative to the predetermined posture, orange may be used for a longer time period associated with the deviation, while an even longer time period associated with the deviation may be rendered in red. Also, blue may be used to alert the user if they are frozen in a particular posture for greater than, for example, 30 seconds. In some embodiments, vibrant primary colors may be used to capture the user's attention from the corner of their eye while they are focused on another task on, for example, display system 108. These colors could be applied to, for example, the text message, the line rendition of the predetermined posture, and the ellipse corresponding to the rendition of the user's face. In some embodiments, the time period associated with changing the colors displayed on graphical image 110 due to lack of user response may range from 2 seconds to 30 minutes. In particular embodiments, the size of graphical image 110 in relation to display system 106 may also be increased in accordance with a user not responding to alerts for a certain time period.

In some embodiments, visual data provided by imaging device 106 may not be of acceptable quality if light levels are low. This limitation may be, for example, due to the small apertures associated with the lens incorporated into imaging device 106. To work around this limitation, a color image from imaging device 106 may be converted into a grayscale image that is processed in a histogram equalization algorithm that balances the darkest and lightest regions of the image to provide a better foundation for cascade classifier face detection algorithms. The grayscale image is again processed in a gamma correction algorithm called gamma compression that lightens the image. In some embodiments, the grayscale image is processed using the Contrast Limited Adaptive Histogram Equalization algorithm that specializes in producing photo realistic image and sensor data in low lighting conditions resulting in an image that can be successfully analyzed by face detection algorithms even in low light conditions. In some embodiments, any combination of image processing algorithms may be used depending on ambient light levels. In particular embodiments, image processing algorithms may be applied individually to the different color channels (e.g., red, green and blue) of a color image to perform operations such as facial recognition or face detection.

Advice may also be given to the user to take a walk or other corrective action if improper posture occurs over a period of time. For example, the system may determine how long a person is sitting in front of a computer and in which posture. So a reminder to stretch, walk, drink, move, etc. can be triggered not just based on a timer (e.g., 35 to 45 minutes); the reminder can be triggered smartly because the system knows how long the user was sitting and the quality of their posture. If the user sits in a bad posture (i.e., they have a hard time holding their own ideal posture) the system can remind the user after a shorter period of time, such as 15 to 20 minutes. On the other hand, if the user maintains their ideal posture, the reminder time can be longer (e.g., 35 to 60 minutes). Also if the user consistently has a hard time sitting in their chosen good posture, the system can ask them to get help with their work station setup or posture they believe to be optimal. Or, posture analysis system 100 may recognize that the user might have changed the position of the computer (camera) or chair, or that the lighting situation has changed so significantly that the software needs to render a new good posture (predetermined posture), necessitating a posture recalibration.

In some embodiments, a user could choose to set posture analysis system 100 to give feedback strictly so that the slightest deviation from good posture results in feedback to the user. Conversely, the user can explicitly set the system to only provide feedback when the user is far out of good posture, a so-called looser interpretation of good posture. In addition, the user could explicitly choose to receive frequent feedback about their posture or explicitly choose to receive infrequent feedback such as at the end of the session, end of the day, end of the week or some other time frame. The system could also determine how strict/loose to set the posture calculation and how frequent/infrequent to give the user feedback from a variety of implicit user factors such as how long the user has used the posture tracking system, how often the user dismisses or ignores feedback, or how fast the user responds to feedback and the like.

Figure 9:
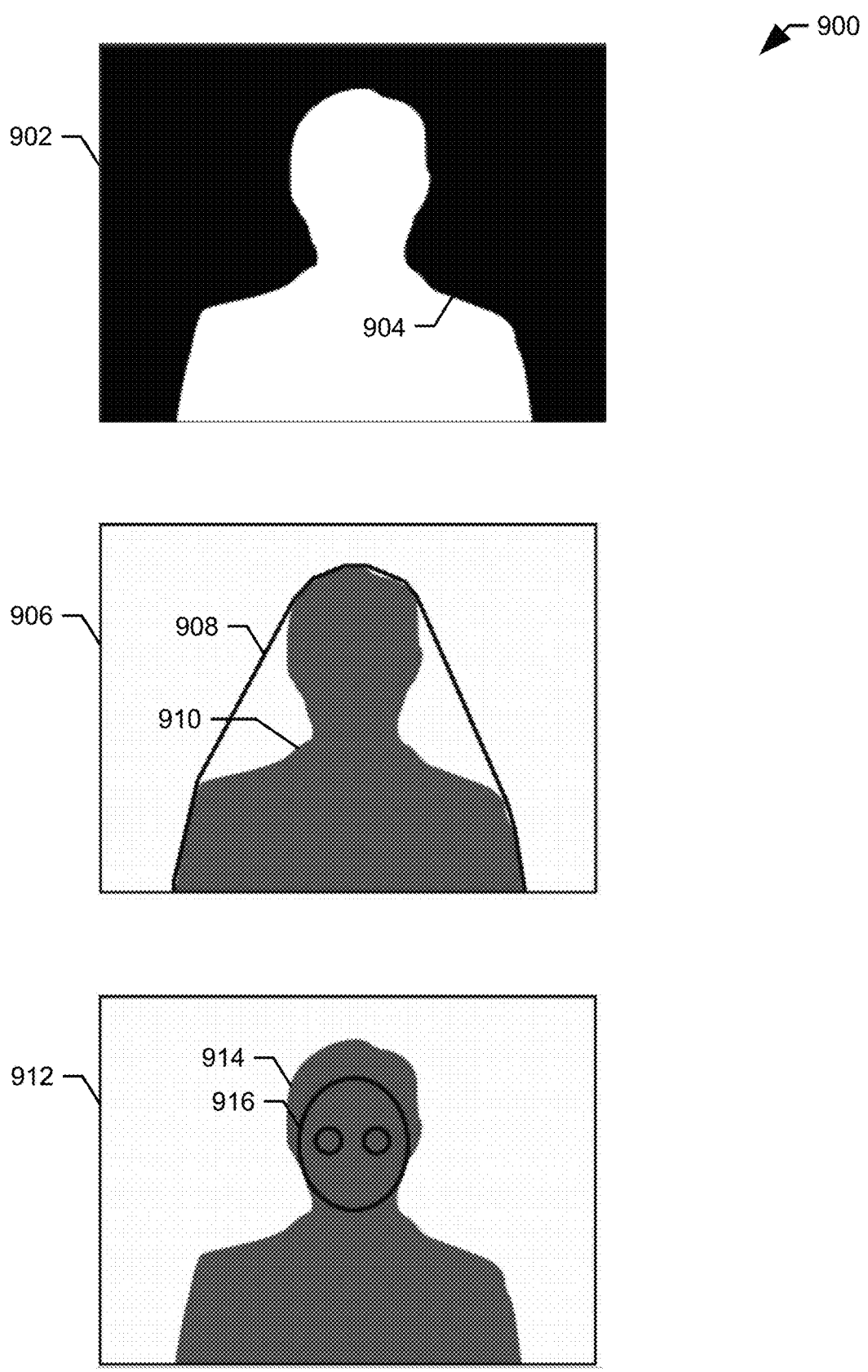
FIG. 9 is a schematic diagram depicting an embodiment of a sequence of frames to determine a user's posture.

FIG. 9 is a schematic diagram depicting an embodiment of a sequence of frames 900 to determine a user's posture. In some embodiments, a frame 902 associated with visual data from imaging device 106 includes a profile 904 of a user that is determined as a foreground mask based on the area of any contours of foreground segments in frame 902. In some embodiments, profile 904 is determined as a largest blob from the foreground, where a user's position is illustrated in a general outline of the person's body and is referred to as a "blob."

In some embodiments, a frame 906 evolves from frame 902, where frame 906 is generated by calculating a convex hull 908 over a largest blob contour 910 associated with the profile 904. A convex hull is defined as a simplified shape of a primary object that is being tracked, in this case the user's posture. In some embodiments, convex hull 908 moves in accordance with any shift in a user's posture. Based on a position of a convex hull associated with a predetermined posture, the instantaneous position of convex hull 908 relative to the position of the convex hull associated with the predetermined posture provides a measure of the associated shift in the user's posture from the predetermined posture. This forms the basis for a posture tracking algorithm. In some embodiments, the largest blob contour may be identical to profile 904.

In some embodiments, additional processing on the visual data associated with frame 906 gives a frame 912 that includes a user profile 914 (which may be identical to profile 904) as well as a detected user face 916. In some embodiments, detected user face 916 may be determined using OpenCV or other algorithms such as frontal face and eye cascades.

Figure 10:
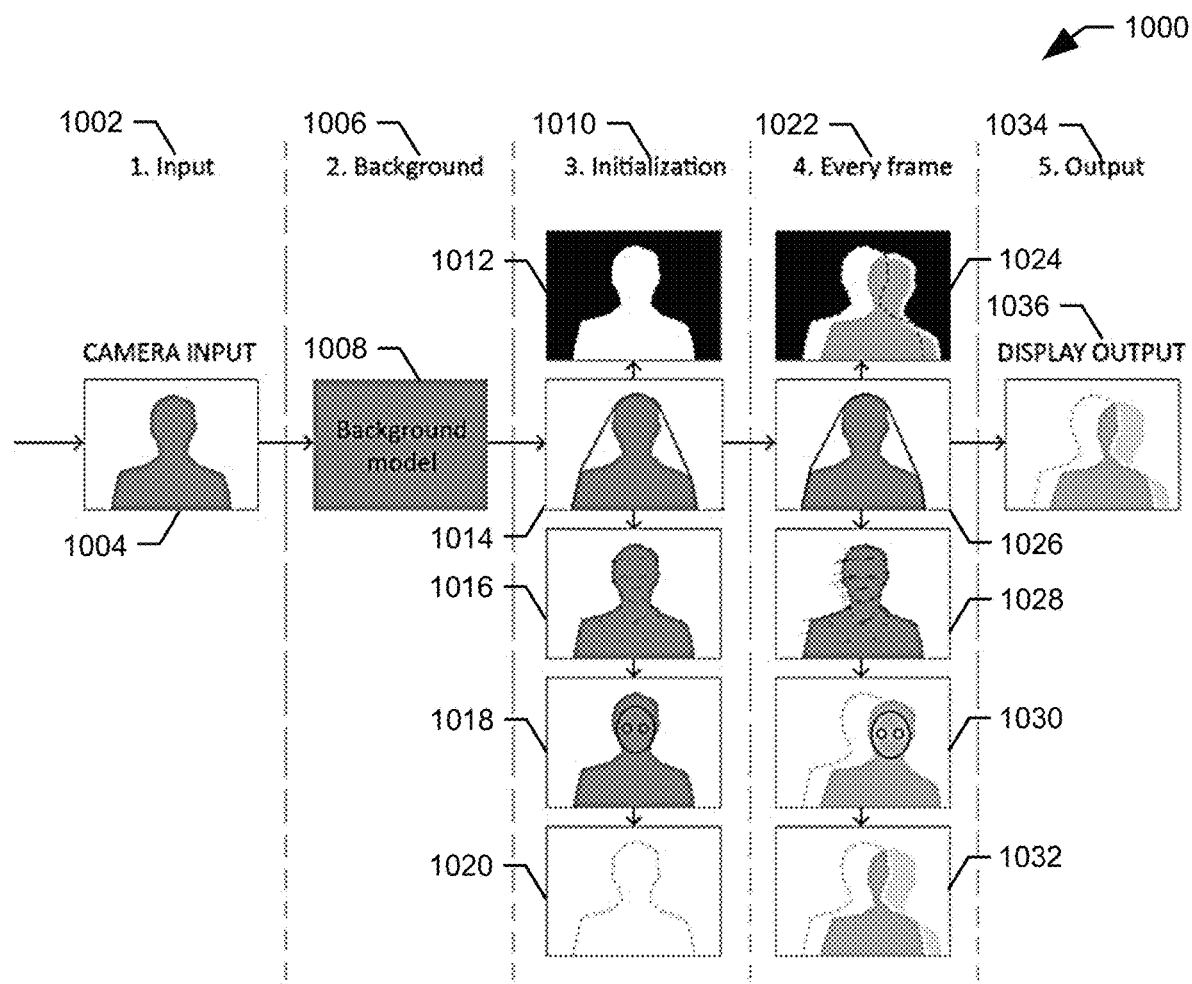
FIG. 10 is a schematic diagram depicting an embodiment of a workflow that illustrates the operation of a posture analysis system.

FIG. 10 is a schematic diagram depicting an embodiment of a workflow that illustrates the operation of posture analysis system 100. During a system initialization process 1002 (denoted by input in FIG. 10), posture analysis system 100 initializes receiving data from imaging device 106. Input from imaging device 106 may be represented by a frame 1004 that may include visual information about a user in the field of view of imaging device 106. In some embodiments, a background initialization step 1006 characterizes a background model 1008 in the absence of the user (i.e., when the user is not in the field of view of imaging device 106). This activity allows posture analysis system 100 to appropriately determine the presence of the user as a foreground element to accomplish posture tracking. In some embodiments, a machine learning classifier may be used to create a background model. In other embodiments, background initialization 1006 may be skipped altogether.

A user initialization step 1010 characterizes a predetermined posture associated with a user. In some embodiments, the user positions themselves in the field of view of imaging device 106 to perform initialization step 1010. In some embodiments, initialization step 1010 includes receiving a frame 1014 containing an image of the user, using image processing techniques (such as convex hull and blob analysis) to generate a frame 1016 containing a convex hull associated with the user's image profile, using face detection and facial detection techniques to confirm a presence of the user's face in a generated frame 1018. Additionally, the system generates a frame 1020 containing an outline of the user's profile, finally generating a frame 1012 that confirms the outline of the user's profile and storing data associated with frame 1012 as the predetermined posture. In some embodiments, the predetermined posture associated with user initialization step 1010 may be determined via professional input such as input from a therapist, ergonomics professional, a coach, in person, or via the internet in a video chat, general information from the Internet, and so on.

A posture tracking step 1022 tracks the user's posture in substantially real time. In some embodiments, the user positions themselves in the field of view of imaging device 106 to perform posture tracking step 1022. In some embodiments, posture tracking step 1022 includes receiving a frame 1026 containing an image of the user, using image processing techniques (such as convex hull and blob analysis) to generate a frame 1028 containing a convex hull associated with the user's image profile. In some embodiments, posture tracking step 1022 uses face detection and facial detection techniques to confirm a presence of the user's face in a generated frame 1030, generating a frame 1030 containing an outline of the user's profile relative to the predetermined posture. Next, posture tracking step 1022 generates a frame 1032 that confirms the outline of the user profile. Finally, posture tracking step 1022 generates a frame 1024 that confirms the outline of the user's profile and current posture relative to the predetermined posture. In some embodiments, posture tracking step 1022 as implemented by posture analysis system 100 may be capable of re-initializing posture tracking of a user even when the user returns after having exited from the field of view of imaging device 106. In some embodiments, posture tracking step 1022 as implemented by posture analysis system 100 can detect a physical movement or other impairment in imaging device 106, and can autonomously recognize the need to redo the background learning and posture calibration steps, without the user needing to take any actions.

In some embodiments, background initialization step 1006, user initialization step 1010, and posture tracking step 1022 may be carried out in any order, not necessarily in the sequence presented in FIG. 10. In some embodiments, posture analysis system 100 may be configured to detect when the user has left the field of view of the camera based on, for example, information stored from background initialization step 1006.

In some embodiments, a user interface presented by posture analysis system 100 may include buttons and a visual display. The visual display may include a live-video display of the scene captured by the camera. If the user is recognized in the scene, a mask is displayed around the user's boundary. The mask is a region of pixels outside the boundary of the user's body as detected by posture analysis system 100, and the region may be blurred such that the background scene appears opaque. In operation, the user's objective is to keep their body within the clear boundary of pixels. Thus, the user may observe a visual image of their current posture in the form of a boundary in which they may position the user's body. When they move out of the boundary, they can be made aware of this as their actual position is shown outside the boundary shown in the image.

The ideal posture can also be indicated by a simple outline or by creating an avatar of the real person inside of the person's outline. The user may then change or otherwise correct their position so that the image of their actual position coincides with the image projected in the visual boundary shown to them. When an optimum position is achieved, the visual representation may indicate that the user is in the proper position, which may change if a user moves. For example, the image may appear bright green when a user is in a preferred position, and may change to red if the user poses outside the boundary of the preferred position. Audible alerts may also be incorporated, alerting the user that their posture is outside the boundaries. The appearance or audible sound of such an alert may be varied depending on the preferred user experience, avoiding annoying alerts that might distract or distress the user.

In some embodiments, an output step 1034 presents posture tracking results to a user via a display output 1036. In some embodiments, display output 1036 is identical to graphical image 110. In some embodiments, an image of the user and an outline of the predetermined posture may be presented. In other embodiments, the image of the user may be replaced with a graphic element such as an ellipse. Depending on the deviation of the user's current posture from the predetermined posture, display output 1036 may show different colors. For example, if the user has assumed the predetermined posture display output 1036 may use a green color for rendering certain elements. If the user deviates from the predetermined posture, display output 1036 may use other colors such as yellow or red, depending on the severity of the deviation.

Posture analysis system 100 can be used to correct posture at a computer desk or working in proximity to any type of display device. Posture analysis system 100 can also be used to guide users in full body postures and movements, if the visual data from imaging device 106 is interpreted and sent to (3D)-video-glasses, helmet-mounted displays, or a fixed monitor, or if the positioning feedback is verbalized and played as audio feedback to the user. Posture analysis system 100 is also useful in situations such as yoga, physical therapy, exercise, stretching, or any other learning of body movement where the sequence and feedback would be at least similar to the posture feedback discussed herein. Other applications include realizations in airplanes, buses, trains, and cars, where the immediate background is fairly static. In these applications, the background may be less relevant with regards to processing functions, and the focus is primarily on the user in front of imaging device 106.

Figure 11A:
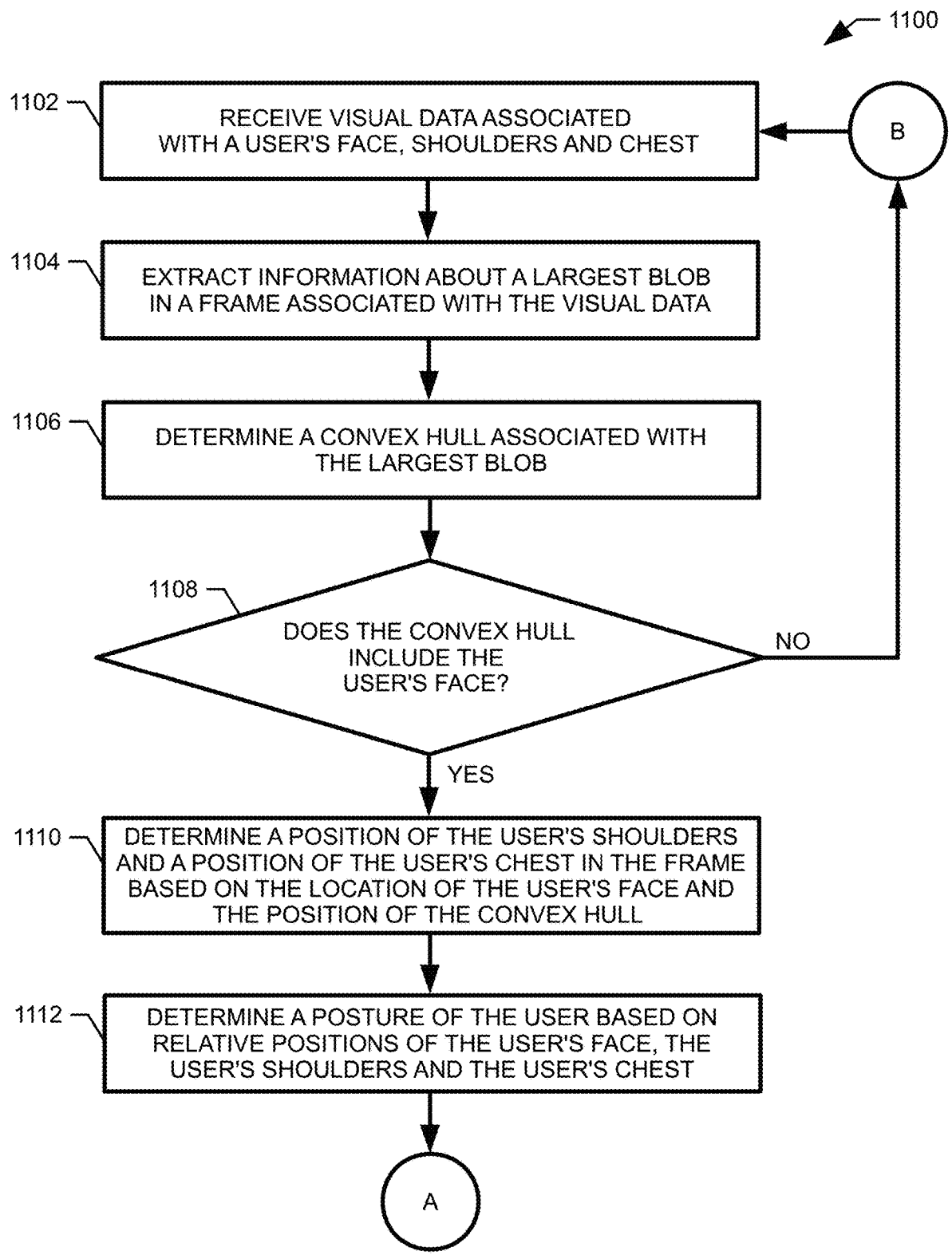
FIGS. 11A and B represent a flow diagram depicting an embodiment of a method to track and correct a user's posture based on image recognition.

FIG. 11A represents a flow diagram depicting an embodiment of a method 1100 to track and correct a user's posture based on image recognition. At 1102 the method receives visual data associated with a user's face, shoulders and chest. In some embodiments, the visual data may be received by processing system 102 from imaging device 106. At 1104, the method extracts information about a largest blob in a frame associated with the visual data. In some embodiments, the largest blob is associated with a foreground rendition of the user in the frame, to include the user's head, shoulders and chest. At 1106, the method determines a convex hull associated with the largest blob, where a convex hull is defined as the smallest convex set that contains all the points of the largest blob. Next, at 1108, the method determines whether the convex hull includes the user's face, using techniques such as facial detection. If the convex hull does not include the user's face then the method goes to B and returns back to 1102, where the system reattempts to detect the presence of the user's face in the visual data. On the other hand if, at 1108, the convex hull includes the user's face then the method goes to 1110, where the method determines a position of the user's shoulders and a position of the user's chest in the frame based on the location of the user's face and the position of the convex hull. Next, at 1112, the method determines a posture of the user based on relative positions of the user's face, the user's shoulders and the user's chest. The method then goes to A, with a continued description in FIG. 11B.

Figure 11B:
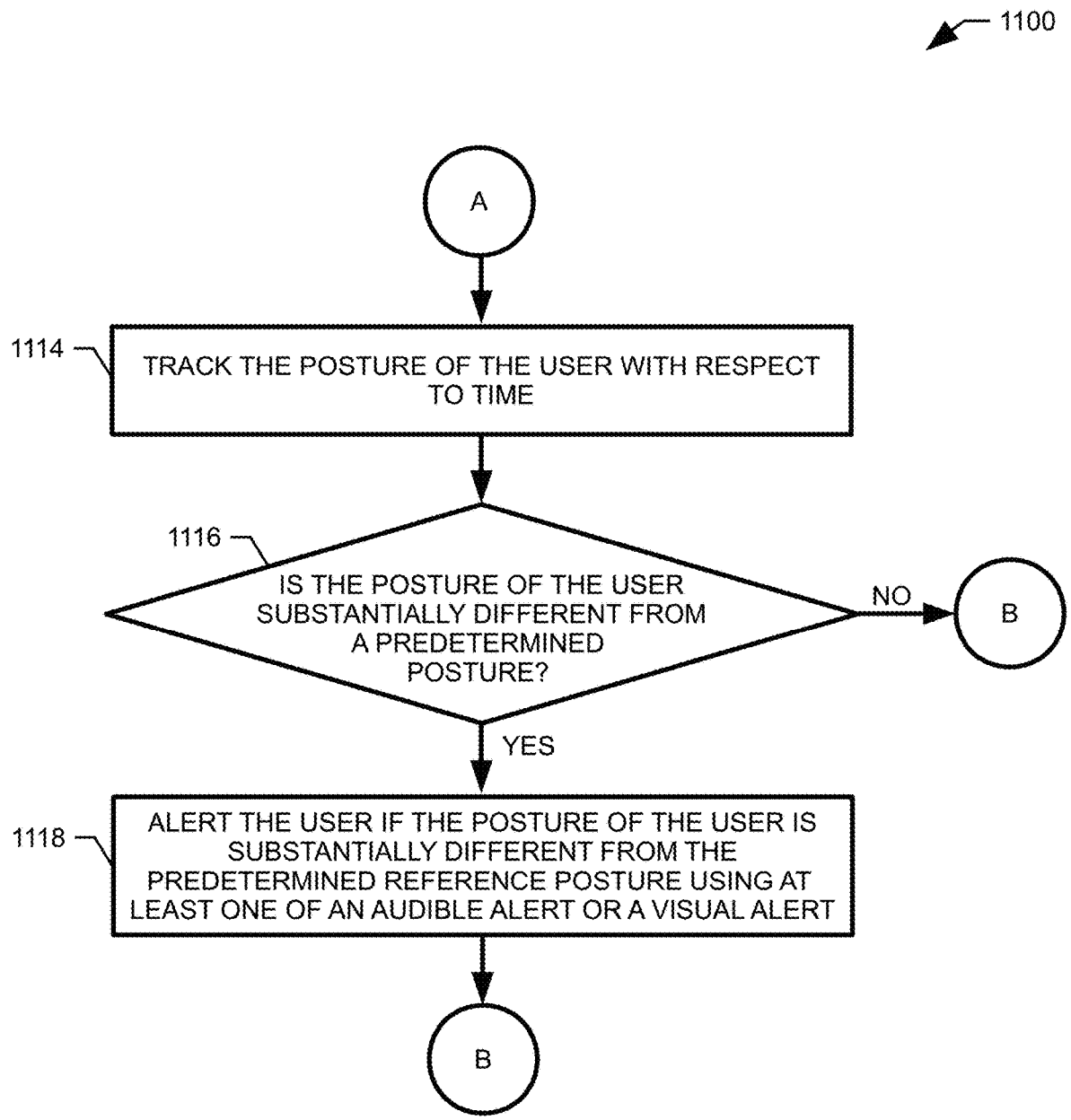

FIG. 11B is a continued description of method 1100. Starting at A, the method goes to 1114, where the method tracks the posture of the user with respect to time using the posture tracking methods described herein. At 1116 the method checks to see whether the posture of the user is substantially different from a predetermined posture. If the posture of the user is not substantially different from the predetermined posture then the method goes to B, and returns back to 1102. On the other hand if, at 1116, the posture of the user is substantially different from the predetermined posture then the method goes to 1118, where the method alerts the user if the posture of the user is substantially different from the predetermined reference posture using at least one of an audible alert or a visual alert.

Figure 12A:
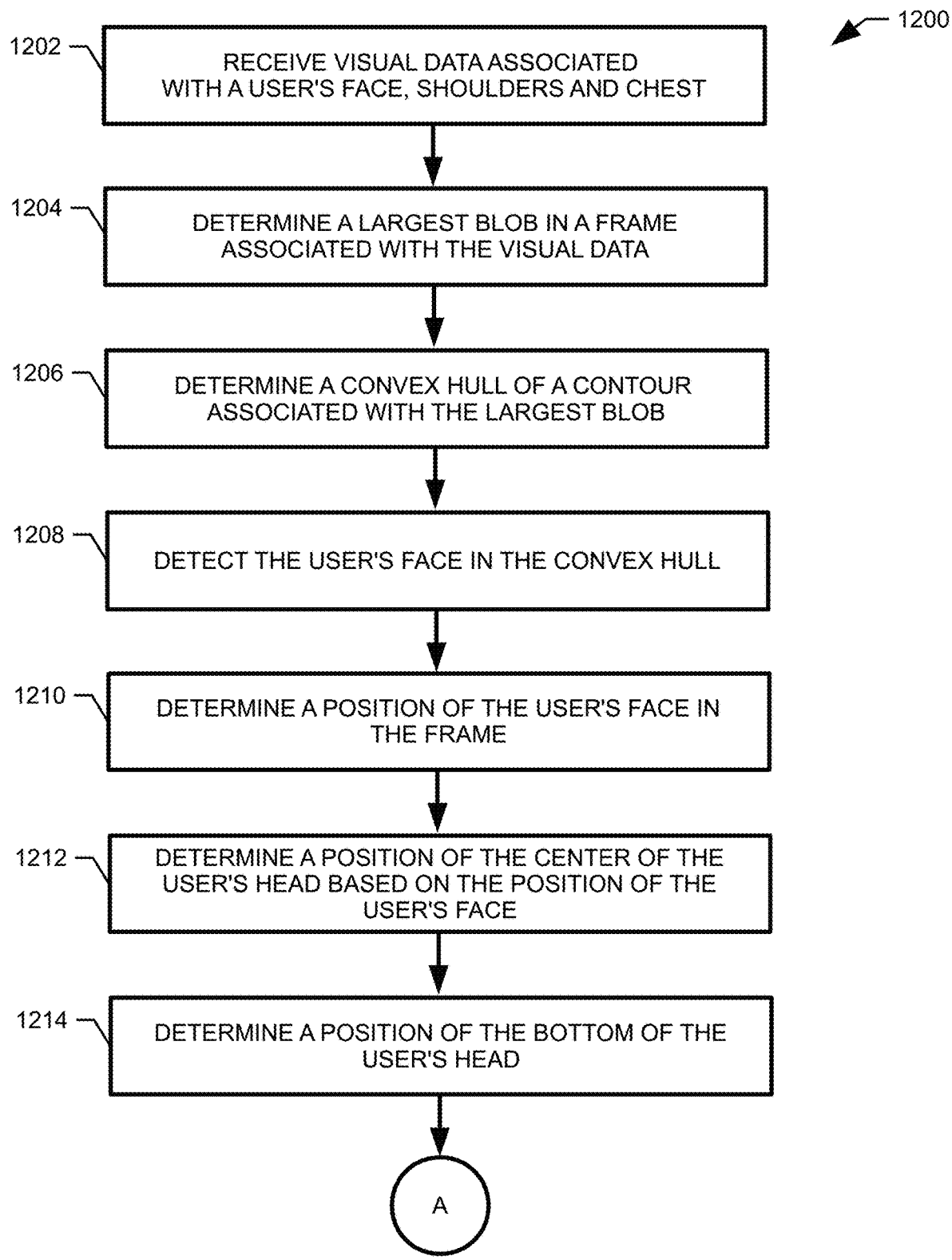
FIGS. 12A and B represent a flow diagram depicting an embodiment of a method to characterize a user's posture.

FIG. 12A represents a flow diagram depicting an embodiment of a method 1200 to characterize a user's posture. At 1202, the method receives visual data associated with a user's head, shoulders and chest. In some embodiments, the visual data may be received by processing system 102 from imaging device 106. At 1204, the method determines a largest blob in a frame associated with the visual data. Next, at 1206, the method determines a convex hull of a contour associated with a largest blob. The process of determining the largest blob and associated convex hull is performed using methods described earlier.

At 1208, the method detects the user's face in the convex hull using, for example, OpenCV or frontal face and eye cascades. Next, at 1210, the method determines the presence of the user's face in the frame. At 1212, the method determines a position of the center of the user's head based on the position of the user's face, while at 1214 the method determines a position of the bottom of the user's head. The method then goes to A, with a continued description provided subsequently.

Figure 12B:
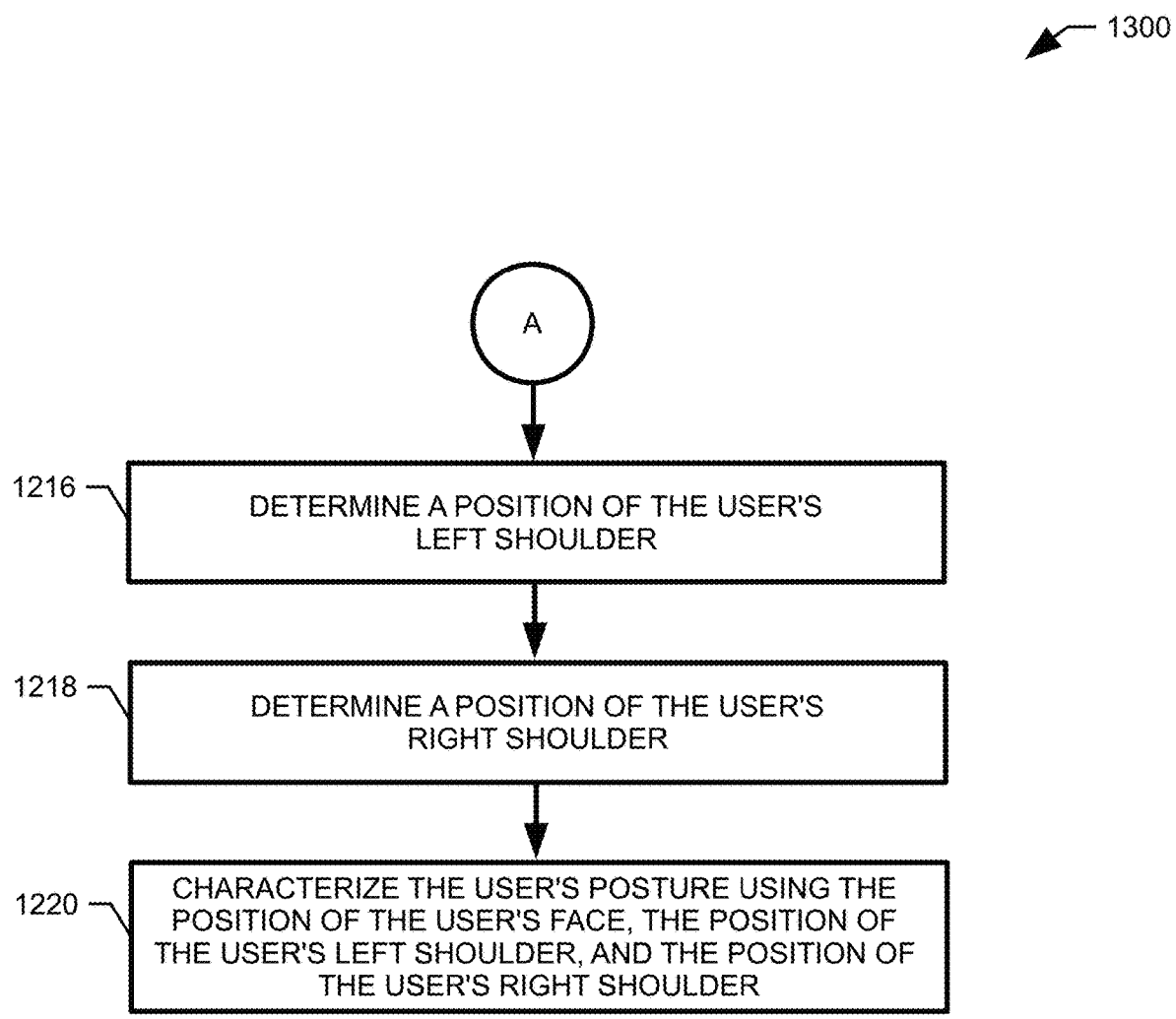

FIG. 12B is a continued description of the method 1200. Starting at A, the method goes to 1216, where the method determines a position of the user's left shoulder based on the convex hull. Next, at 1218, the method determines a position of the user's right shoulder based on the convex hull. In some embodiments, the position of the user's left shoulder and the position of the user's right shoulder are determined based on user motion, with the user swaying side-to-side. Using image recognition or computer vision algorithms, the user's left shoulder is located by finding the center of the user's head and the bottom of the user's head within the user motion region and then splitting the user motion region in half wherein the left side portion of the user motion region located beneath the head and to the left of the center of the head is considered the left shoulder. Though this region will contain non-shoulder data due to the user movement, it will still be able to use this shoulder data to find the shoulder in the posture tracking step. Similarly, the user's right shoulder is located by finding the center of the user's head and the bottom of the user's head within the user motion region and then splitting the user motion region in half wherein the right side portion of the user motion region located beneath the head and to the right of the center of the head is considered the right shoulder. Though this region will contain non-shoulder data due to the user movement, it will still be able to use this shoulder data to find the shoulder in the posture tracking step.

Finally, at 1220, the method characterizes the user's posture using the position of the user's face, the position of the user's left shoulder, and the position of the user's right shoulder.

Figure 13:
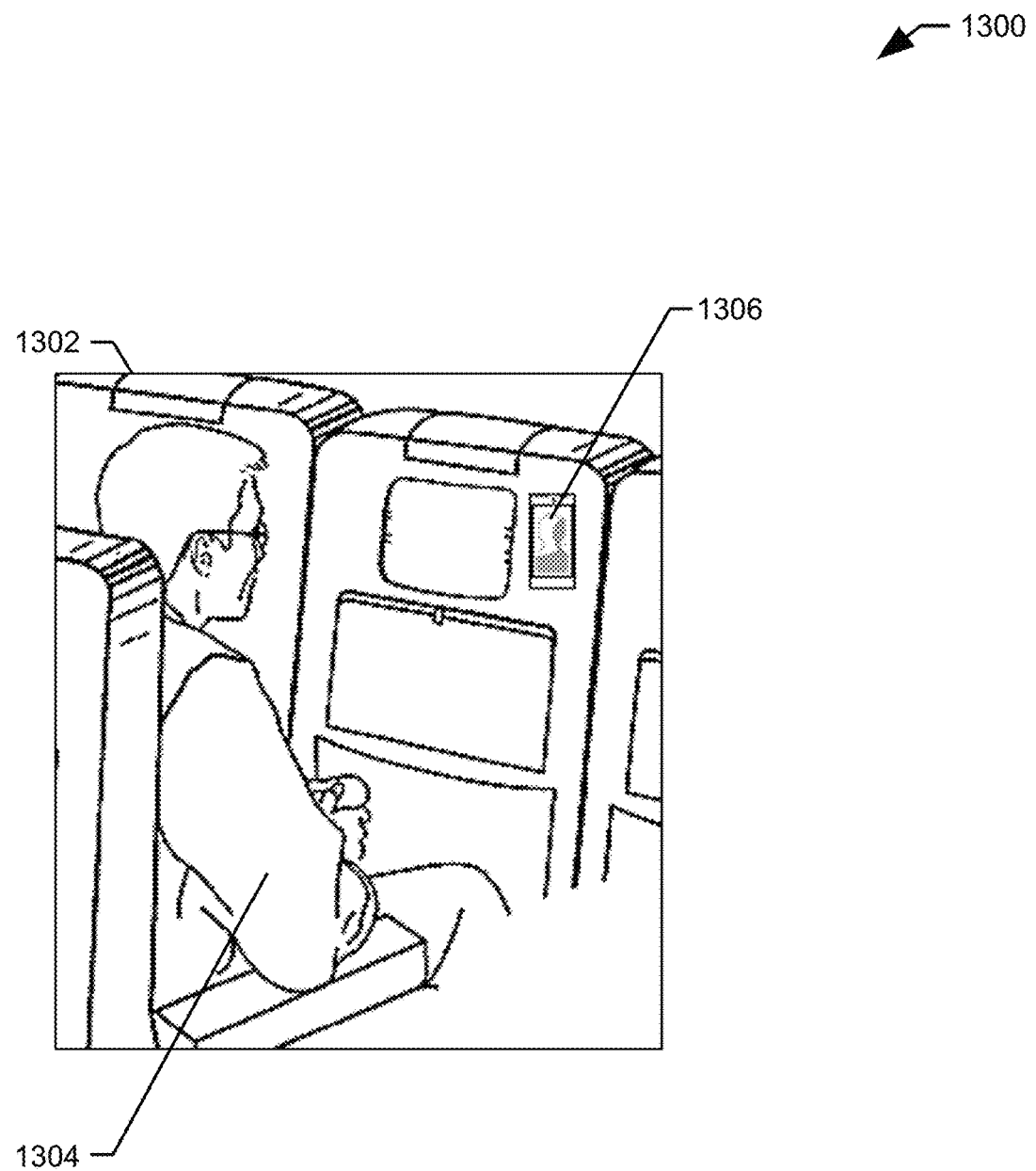
FIG. 13 is a schematic diagram illustrating an embodiment of an application of a posture tracking system.

FIG. 13 is a schematic diagram illustrating an embodiment of an application 1300 of posture tracking system 100 in an airplane cabin 1302. In some embodiments, a user 1304 may install and run posture tracking system 100 on a mobile device 1306 and place (or mount) the mobile device on the back of the seat in front of the user as shown in FIG. 13. In some embodiments, a user mobile device such as a mobile phone or a tablet may be mounted on the back of the seat in front of the user using plastic clips. In some embodiments, a user may place their laptop computer with integrated webcam on top of a tray table in front of the user. User 1304 may initialize posture tracking system 100 with a predetermined posture using the built-in camera of mobile device 1306. Then, posture tracking system 100 can track the posture of user 1304 for the period of the journey or for a time period specified by the user.

Figure 14:
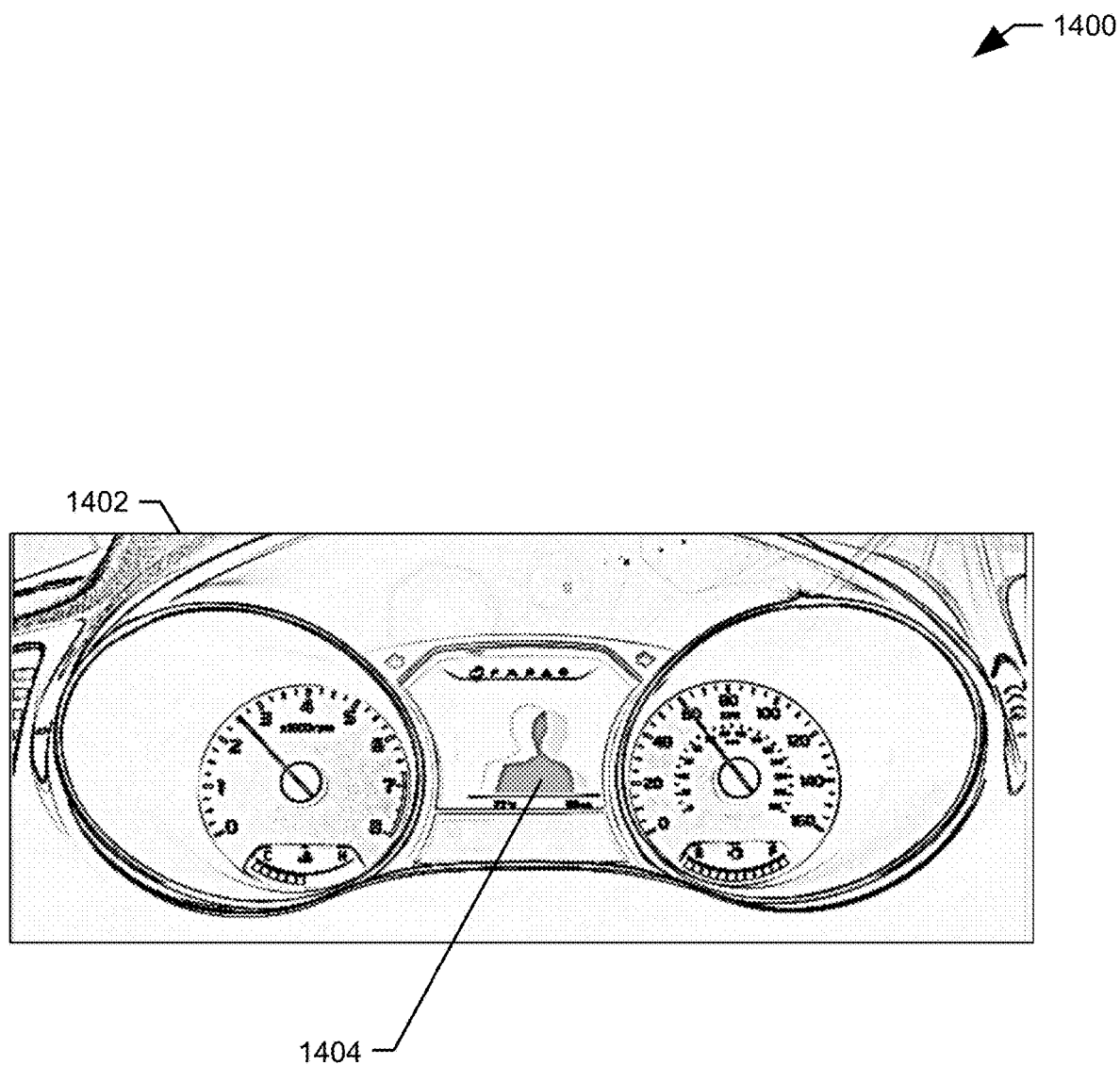
FIG. 14 is a schematic diagram illustrating an embodiment of another application of a posture tracking system.

FIG. 14 is a schematic diagram illustrating an embodiment of another application 1400 of posture tracking system 100 in an automobile or other vehicle to provide a posture tracking feature for the driver of the automobile. FIG. 14 shows a vehicle instrument cluster 1402, with posture tracking system 100 providing posture feedback to a driver of the vehicle on a vehicle display 1404. Some embodiments may use a mounted camera on the vehicle dashboard in front of the user to monitor the user's posture, while some embodiments may use a camera that is installed in the vehicle dashboard to monitor the user's posture.

Other embodiments of posture analysis system 100 may include an implementation in an operating room where an imaging device is focused on the doctor or other personnel and is coupled to a computing system and associated display device to provide posture feedback to the doctor or other personnel. This system would provide feedback for situations such as when a user's shoulders are not square to the floor for extended time (shrugging). Also a user having their arms in fixed positions for long periods of time (either totally straight or elbows bent) may be addressed by posture analysis system 100. General slouching (downward movement of body from an initial good posture position) may also be accounted for. The imaging device facing the doctor could be a laptop or webcam or phone/tablet placed on a moveable arm tray positioned above the patient in the line of sight of the doctor, or anywhere that is doctor facing as long as the doctor's face is within the field of view of the imaging device.

Although the present disclosure is described in terms of certain example embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the scope of the present disclosure.

The invention claimed is:

1. A method comprising:
  receiving, by a computing system, visual data associated with a user;
  determining the user's current posture in three dimensions based on the visual data, wherein determining the user's current posture includes:
    determining the user's posture along a first axis based on a size of the user's face;
    determining the user's posture along a second axis based on a first position of the user's face along the second axis; and
    determining the user's posture along a third axis based on a second position of the user's face along the third axis;
  identifying, by the computing system, a deviation of a user's posture from a predetermined posture based on determining the user's current posture in three dimensions; and
  associating the deviation of the user's posture with a task being performed by the user.

2. The method of claim 1, further comprising recording a history corresponding to the association of the deviation of the user's posture with the specific task.

3. The method of claim 1, wherein the task includes the user using an application executing on the computing system.

4. The method of claim 1, wherein the task is any of reading a book, writing, riding in a vehicle, performing surgery in an operating room, practicing yoga, or any other kind of activity.

5. The method of claim 1, further comprising informing the user when the deviation exceeds a predetermined threshold.

6. The method of claim 5, wherein the informing is performed in substantially real time.

7. The method of claim 5, wherein the informing includes:
  displaying a graphical image depicting the predetermined posture and simultaneously displaying a current representation of the user's posture; and
  providing instructions to the user to correct the user's posture, wherein the instructions include at least one of a textual message, a graphical symbol, audio feedback, or shading a portion of the graphical image, based on the deviation.

8. The method of claim 7, further comprising color-coding the instructions based on a time duration associated with the deviation.

9. The method of claim 7, further comprising:
  determining, based on visual data associated with the user, whether the user has corrected their posture; and
  removing the graphical image responsive to determining that the user has corrected their posture.

10. The method of claim 5, further comprising providing a congratulatory message to the user when the deviation has been corrected.

11. An apparatus comprising:
  an imaging device configured to capture visual data associated with a user; and
  a computing system configured to:
    receive visual data associated with the user;
    determine the user's current posture in three dimensions based on the visual data, wherein determining the user's current posture includes:
      determining the user's posture along a first axis based on a size of the user's face;
      determining the user's posture along a second axis based on a first position of the user's face along the second axis; and
      determining the user's posture along a third axis based on a second position of the user's face along the third axis;
    identify a deviation of a user's posture from a predetermined posture based on determining the user's current posture in three dimensions; and
    associate the deviation of the user's posture with a task being performed by the user.

12. The apparatus of claim 11, further comprising a memory configured to store historical data corresponding to the deviation of the user's posture with the specific task.

13. The apparatus of claim 11, wherein the task includes the user using an application executing on the computing system.

14. The apparatus of claim 11, wherein the task is any of reading a book, writing, riding in a vehicle, performing surgery in an operating room, practicing yoga, or any other kind of activity.

15. The apparatus of claim 11, the computing system informs the user when the deviation exceeds a predetermined threshold.

16. The apparatus of claim 15, wherein the information is presented on a visual display.

17. The apparatus of claim 15, wherein the information is presented in substantially real time.

18. The apparatus of claim 15, wherein the computing system is configured to:
  display a graphical image depicting the predetermined posture while simultaneously displaying a current representation of the user's posture; and
  provide instructions to the user to correct the user's posture, wherein the instructions include at least one of a textual message, a graphical symbol, audio feedback, or shading a portion of the graphical image, based on the deviation.

19. The apparatus of claim 18, wherein the computing system is configured to color-code the instructions based on a time duration associated with the deviation.

20. The apparatus of claim 18, wherein the computing system is configured to:
  determine, based on visual data associated with the user, whether the user has corrected their posture; and remove the graphical image responsive to determining that the user has corrected their posture.

21. The apparatus of claim 15, wherein the computing system is configured to provide a congratulatory message to the user when the deviation has been corrected.

\* \* \* \* \*